(12) United States Patent
Kilbey

(10) Patent No.: US 12,390,362 B2
(45) Date of Patent: *Aug. 19, 2025

(54) UNIVERSAL WRAP FOR SECURING A THERMAL PACK

(71) Applicant: Bryan E. Kilbey, DeFuniak Springs, FL (US)

(72) Inventor: Bryan E. Kilbey, DeFuniak Springs, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 18/609,518

(22) Filed: Mar. 19, 2024

(65) Prior Publication Data
US 2024/0245551 A1 Jul. 25, 2024

Related U.S. Application Data

(63) Continuation of application No. 18/100,721, filed on Jan. 24, 2023, now Pat. No. 11,931,289, which is a continuation of application No. 16/537,678, filed on Aug. 12, 2019, now Pat. No. 11,559,427.

(51) Int. Cl.
*A61F 7/02* (2006.01)
*A61F 7/00* (2006.01)
*A61F 13/14* (2006.01)

(52) U.S. Cl.
CPC ........ *A61F 7/02* (2013.01); *A61F 2007/0022* (2013.01); *A61F 2007/0023* (2013.01); *A61F 2007/0024* (2013.01); *A61F 2007/0027* (2013.01); *A61F 2007/0226* (2013.01); *A61F 2007/0228* (2013.01); *A61F 13/148* (2013.01)

(58) Field of Classification Search
CPC .................... A61F 13/14; A61F 13/148; A61F 2007/0022; A61F 2007/0024–0027; A61F 2007/0228; A61F 2007/0231
See application file for complete search history.

(56) References Cited

U.S. PATENT DOCUMENTS

| | | | | |
|---|---|---|---|---|
| 11,559,427 B2* | 1/2023 | Kilbey | ...................... | A61F 7/02 |
| 11,931,289 B2* | 3/2024 | Kilbey | ...................... | A61F 7/02 |
| 2021/0045914 A1* | 2/2021 | Kilbey | ...................... | A61F 7/02 |

* cited by examiner

*Primary Examiner* — Kaitlyn E Smith
(74) *Attorney, Agent, or Firm* — J. Wiley Horton

(57) ABSTRACT

A system and method for providing a universal wrap that can apply a thermal pack to many different regions of a patient's body. The universal wrap is provided in a standardized form. The medical provider is provided with options to modify the standardized form in order to adapt the wrap to many different applications.

20 Claims, 27 Drawing Sheets

UNIVERSAL WRAP FOR SECURING A THERMAL PACK

CROSS-REFERENCES TO RELATED APPLICATIONS

This application is a continuation of U.S. patent application Ser. No. 18/100,721, now issued as U.S. Pat. No. 11,931,289, which was itself a continuation of U.S. patent application Ser. No. 16/537,678, now issued as U.S. Pat. No. 11,599,427. This application lists the same inventor as the parent applications.

STATEMENT REGARDING FEDERALLY SPONSORED RESEARCH OR DEVELOPMENT

Not Applicable

MICROFICHE APPENDIX

Not Applicable

BACKGROUND OF THE INVENTION

1. Field of the Invention

This invention relates to the field of medical products. More specifically, the invention comprises a wrap that can be used to secure a thermal pack against a selected portion of a patient's anatomy.

2. Description of the Related Art

Thermal packs are used in a wide variety of medical therapies. The term "thermal pack" should be understood to include any device intended to transfer heat to a patient's body or to remove heat from a patient's body. Examples include ice packs, cold gel packs, and hot packs.

There are numerous prior art examples of strap and wrap devices configured to hold a thermal pack against a specific anatomical region. There are wraps designed to press a thermal pack against a patient's knee. There are different designs intended to hold a thermal pack against a patient's ankle. Each of these designs are functionally dissimilar. Each works well for its intended application but lacks the flexibility to accommodate a different application.

Therapy based on heat transfer must often be applied shortly after an injury occurs. This is particularly true for cold therapy, where the efficacy is greatest in the few hours immediately following an injury. Thus, a medical practitioner needs to have the ability to apply a wrap upon the presentation of an injured patient. It is not practical to order a specialized wrap and then wait a day or more for its delivery. It is also impractical to stock a wide range of specialized wraps so that a suitable wrap for any type of injury is always on hand. A more versatile wrap is needed, so that a provider can stock one type of wrap and adopt it to various injuries as needed. The present invention provides such a solution.

BRIEF SUMMARY OF THE PRESENT INVENTION

The present invention comprises a system and method for providing a universal wrap that can apply a thermal pack to many different regions of a patient's body. The universal wrap is provided in a standardized form. The medical provider is provided with options to modify the standardized form in order to adapt the wrap to many different applications.

Figure 1:
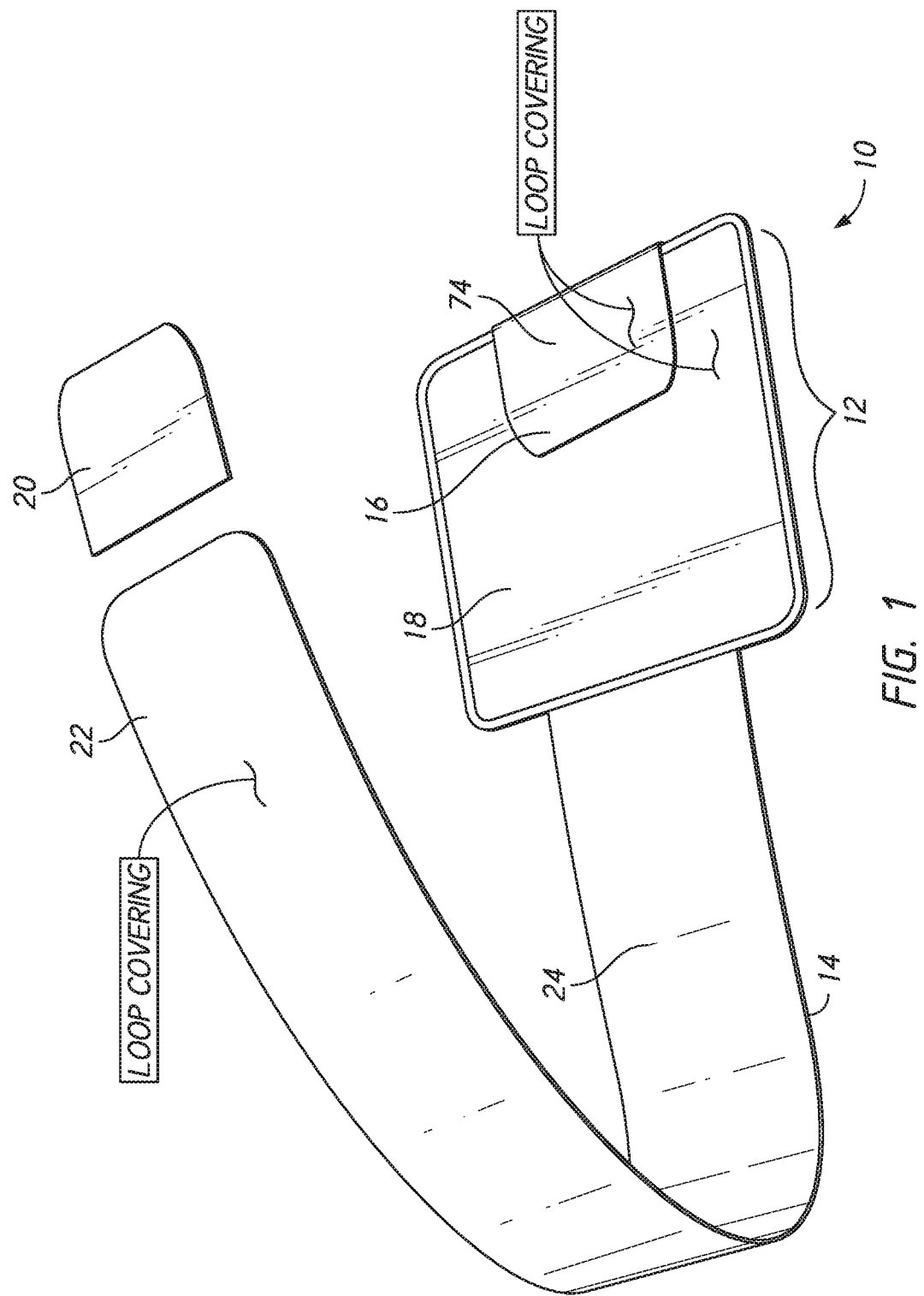
FIG. 1 is a perspective view, showing a wrap assembly made according to the present invention.

REFERENCE NUMERALS IN THE DRAWINGS 10 universal wrap
12 body
14 strap 15 outer surface
16 tab
18 inner surface
20 hook panel
22 outer surface
24 inner surface
26 hook surface
28 hook surface
30 cut
32 first segment
34 second segment
36 thermal pack
38 inner layer
40 outer layer
42 expansion valve
44 hook panel
45 inner sealing layer
46 hook panel
48 bulk thermal media
49 interior volume
50 sub-bag
51 sealed seam
52 first panel
54 second panel
56 outer surface
58 indicating area
60 inner surface
62 sealed perimeter
64 cut
65 patient
66 cut
67 lumbar region
68 knee
70 ankle
72 interior volume
74 back surface

DETAILED DESCRIPTION OF THE INVENTION

FIG. 1 shows an embodiment of the wrap used in the present invention. The various features and options of the wrap will be explained initially. Then an explanation of how these features and options may be used to secure the wrap to a patient will be provided.

Universal wrap 10 includes a flat and rectangular body 12. The body has two lateral edges. Strap 14 attaches to a first lateral edge and extends away from the body as shown. Tab 16 connects to the second lateral edge. In FIG. 1, tab 16 is shown folded over and secured to inner surface 18 of body 12. Inner surface 18 is covered in loop covering. The side of tab 16 facing away from the viewer is covered in hooks. Thus, pressing tab 16 against inner surface 18 secures the tab to the inner surface. Back surface 74 of tab 16 is provided with a loop covering so that other hook panels may be secured to it.

In the context of this disclosure the term "loop covering" means any hook-compatible material. In other words, any fabric to which a hook panel can be secured when using hook-and-loop fasteners. An example of hook-and-loop fasteners is VELCRO brand materials such as marketed by Velcro, BVBA. As those skilled in the art will know, many hook-compatible fabrics are soft and smooth in appearance. They do not necessarily include coarse pile-type loops such as commonly used several decades ago (though the term hook-compatible material would certainly include coarse pile-type loops as well).

Strap 14 has outer surface 22 and inner surface 24. Outer surface 22 is provided with a loop covering as well. Hook panel 20 includes a hook surface—facing away from the viewer in FIG. 1. Hook panel 20 can be secured to the distal end of strap 14 by pressing the hook panel onto outer surface 22—as will be explained subsequently.

Figure 2:
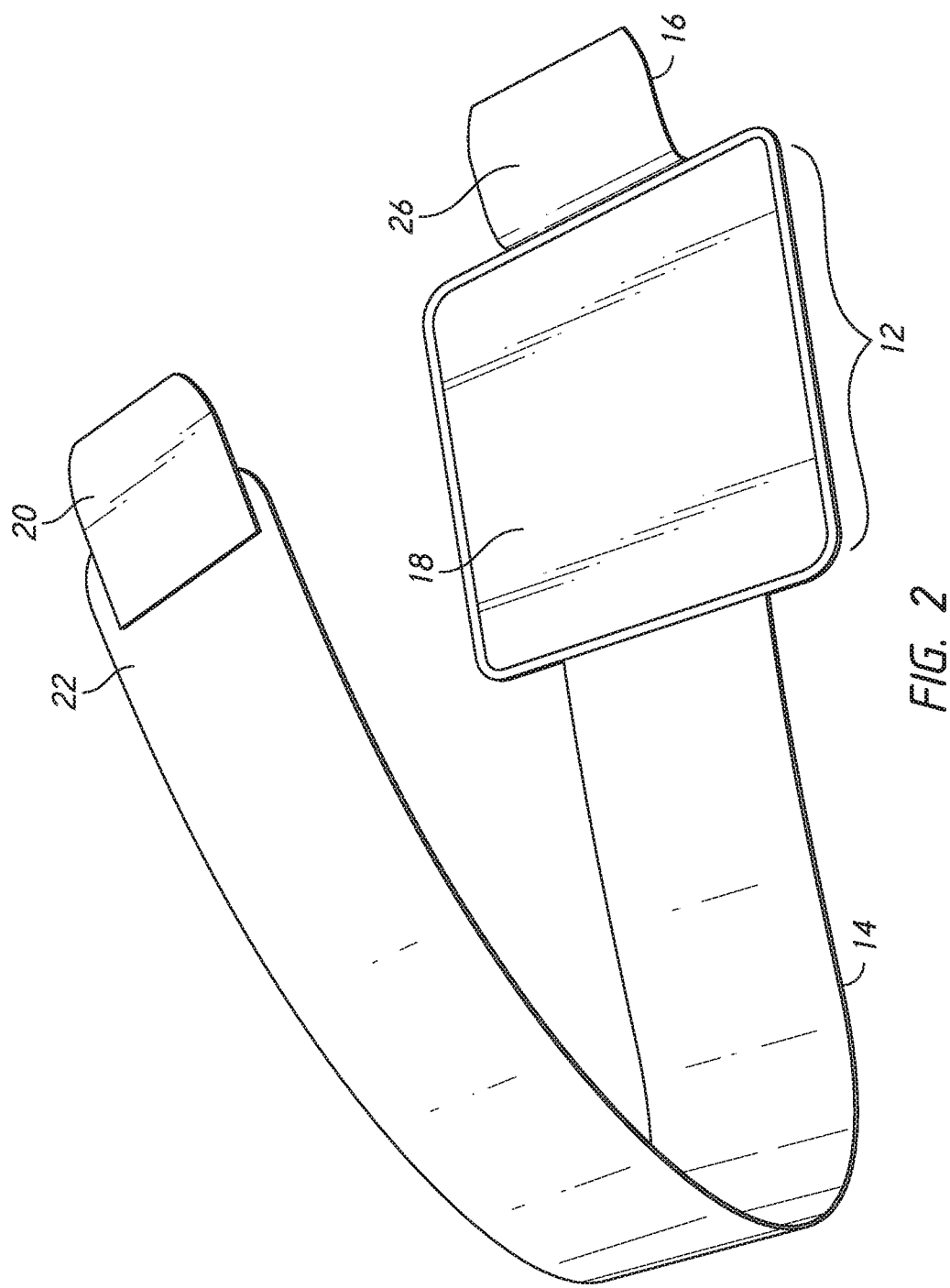
FIG. 2 is a perspective view, showing the wrap of FIG. 1 with a tab in the open position.

FIG. 2 shows the same universal wrap with tab 16 flipped open to reveal hook surface 26. One edge of tab 16 remains attached to the second distal edge of body 12 as shown. Soft fabrics are preferably used for many of the components of the wrap. Body 12 in this embodiment is an assembly of multiple layers. These layers can be assembled by sewing. It is preferable, however, to join the layers by laminating. A laminated assembly can be cut to a reduced side without the trimmed edges fraying or separating. In the example shown in FIG. 2, a bias band is attached around the perimeter of body 12. A stitch line can be used to connect the bias band and if this is present the stitch line also attaches the proximal end of strap 14 and the attached edge of tab 16. Adhesives or lamination techniques can also be used to assemble these components if desired.

Figure 3:
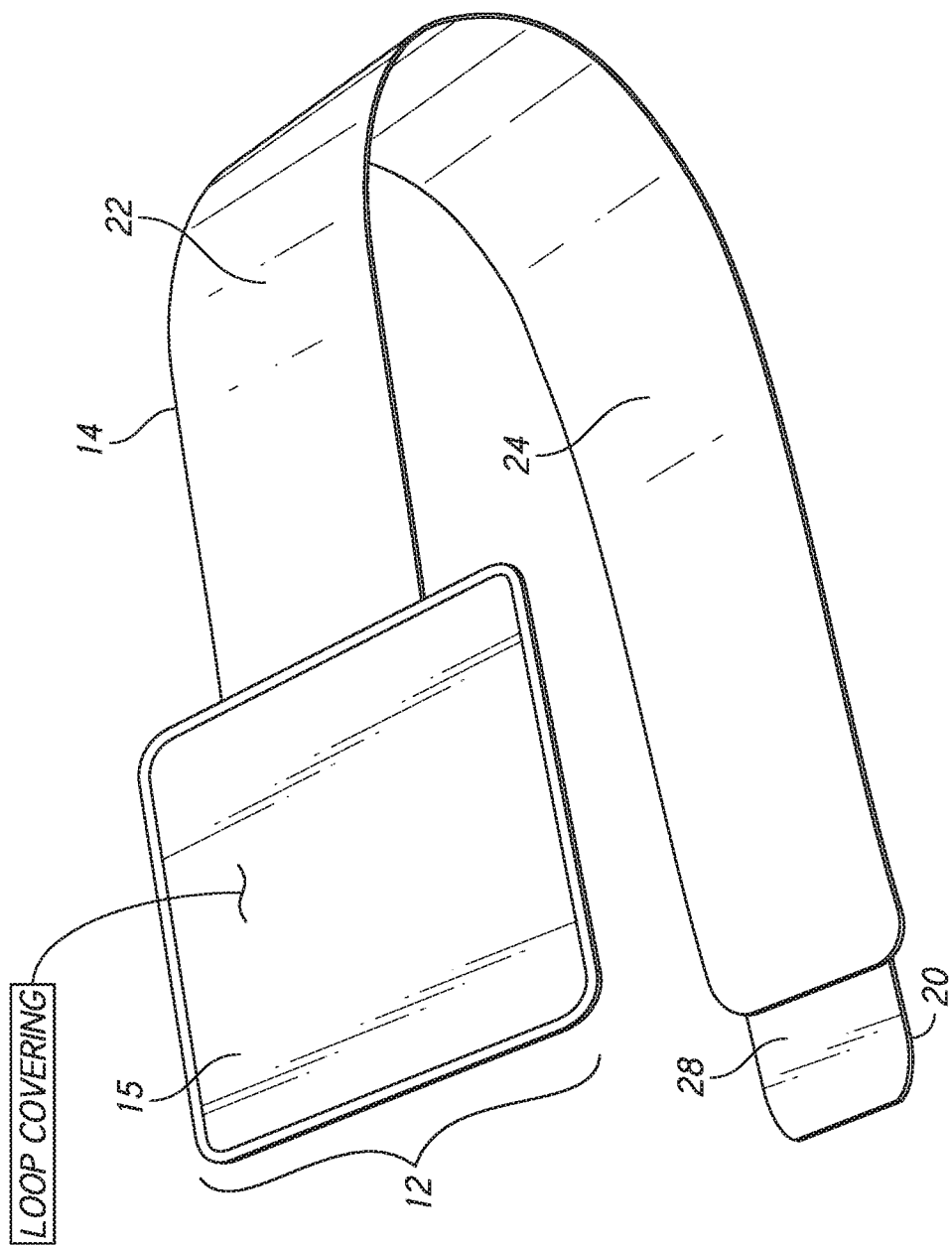
FIG. 3 is a perspective view, showing the configuration of FIG. 1 from a different vantage point.

FIG. 3 shows the assembly of FIG. 1 from a different vantage point. In this view outer surface 15 of body 12 is shown. This outer surface is preferably provided with a loop covering. The reader can also see how hook panel 20 is attached to the distal end of strap 14 by pressing hook surface 28 against outer surface 22. The hooks on hook surface 28 engage the loop covering of outer surface 22 and hold the hook panel in place. The reader will also note how only approximately half of hook panel 20 has been pressed onto strap 14—leaving the balance of the hook panel free. The free portion of hook surface 28 can be pressed onto another loop covered surface. Hook panel 20 thereby becomes a connector.

The fabric used for strap 14 preferably has the following properties: (1) It is elastic so that a degree of stretch and compression can be applied to secure the wrap, (2) At least inner surface 24 is smooth and comfortable for wearing against a patient, and (3) The band may be cut without creating a frayed or unstable edge. This third preferred property allows the wrap to be fitted to a wide variety of patients. Strap 14 is provided in a long un-stretched length, such as 42 inches (107 cm). This can accommodate large patients, but will be too long for smaller patients. The user can cut strap 14 to a shorter length and move hook panel 20 to the newly created distal end.

Figure 4:
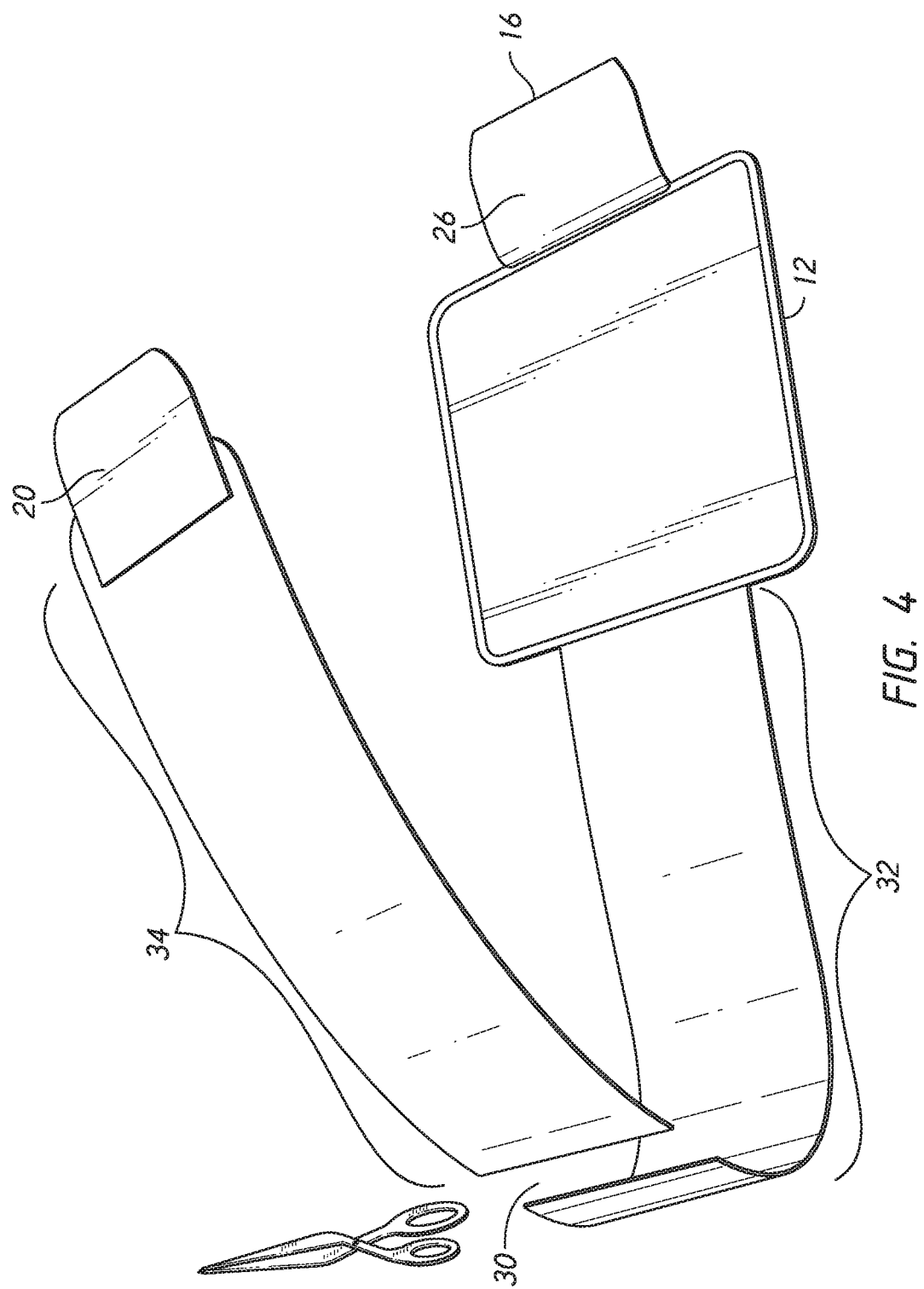
FIG. 4 is a perspective view, showing an alteration to the standard configuration.
Figure 5:
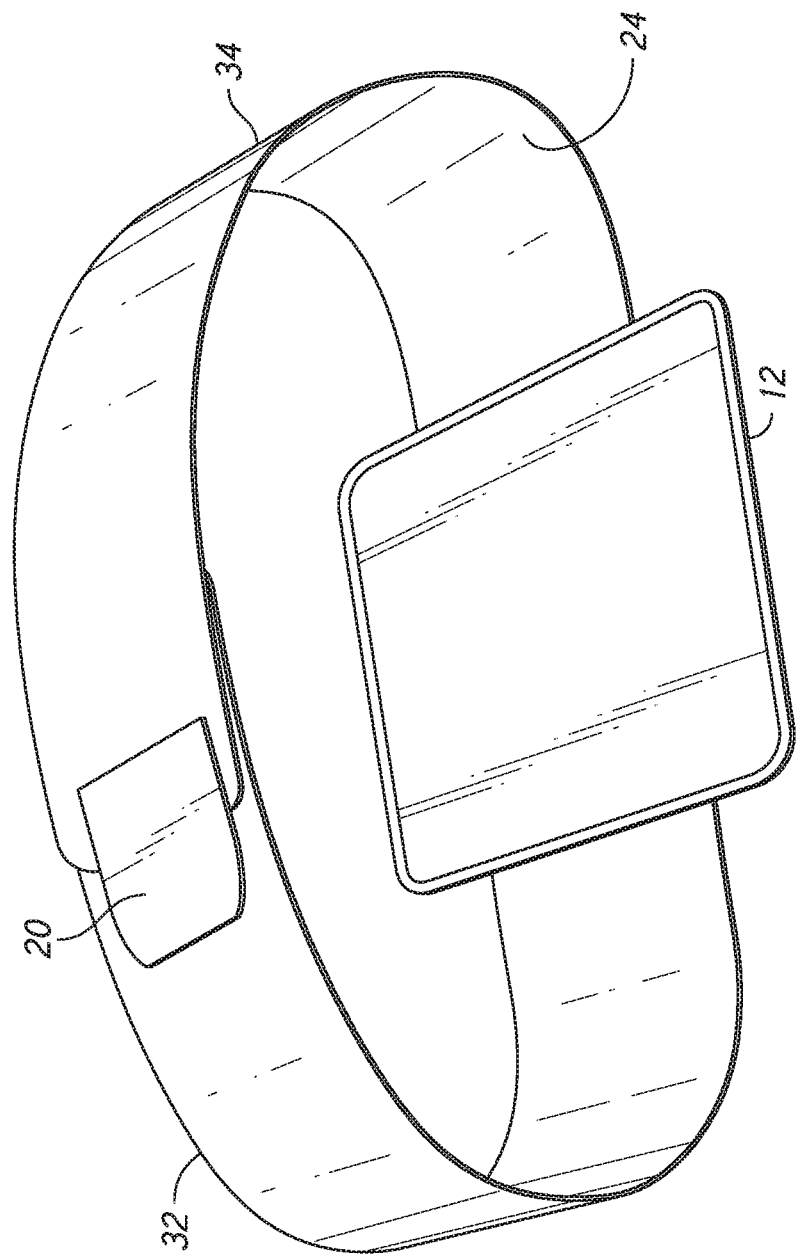
FIG. 5 is a perspective view, showing the configuration of FIG. 4 in an assembled state.
Figure 6:
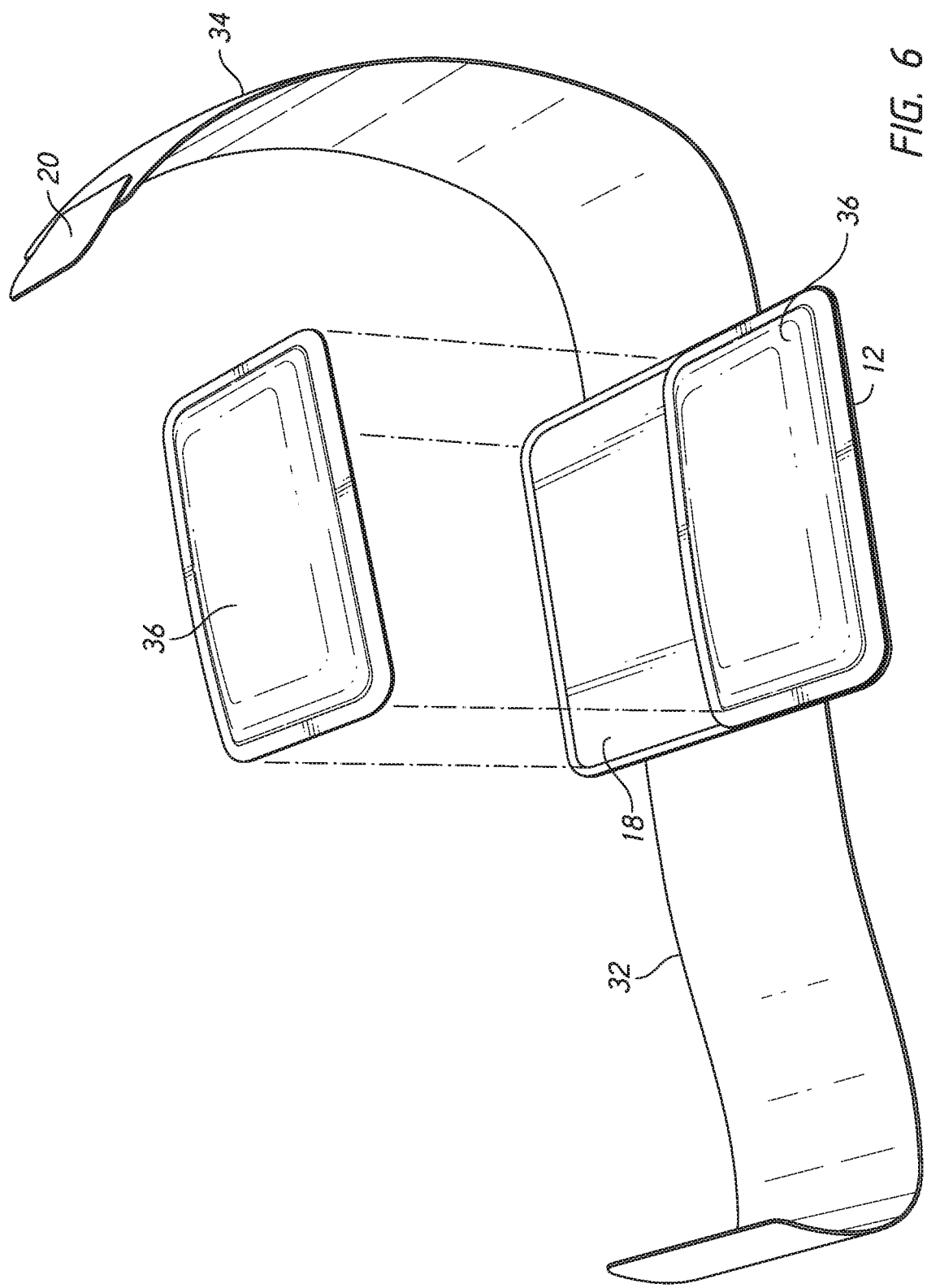
FIG. 6 is a perspective view, showing the addition of a pair of thermal packs.

FIGS. 4-6 show an additional configuration that provides added flexibility. In FIG. 4, strap 14 has been cut along 30 to create first segment 32 and second segment 34. The proximal end of first segment 32 remains attached to body 12. A newly-created distal end for first segment 32 lies at cut 30. Second segment 34 has a newly created proximal end at cut 30. Hook panel 20 remains affixed to the distal end of second segment 34 (though the hook panel can of course be removed at any time by pulling it free).

Second segment 34 is typically flipped over and its proximal end is then placed over tab 16. The proximal end is then pressed down onto the exposed hook surface 26 of tab 16. The loop covering on the outer surface of second segment 34 engages the hook surface on the tab and the second segment is thereby secured. FIG. 5 shows this configuration—with second segment 34 secured in place. Second segment 34 can then be looped over first segment 32 as shown. The exposed portion of hook panel 20 is pressed into the loop covering on first segment 32. A secure and adjustable band is thereby formed. This band can be used to hold body 12 against a selected area of a patient.

Of course, a central purpose of the universal wrap is to hold a thermal pack in position. FIG. 6 shows the universal wrap in the configuration of FIG. 5, but with the band opened by unhooking hook panel 20 from first segment 32. As explained previously, inner surface 18 of body 12 is provided with a loop covering. This loop covering is used to attach one or more thermal packs 36.

In the example of FIG. 6, the thermal packs are provided in a rectangular form. Each thermal pack has one or more hook panels that engage the loop covering on inner surface 18 when the thermal pack is pressed against inner surface 18.

Figure 7:
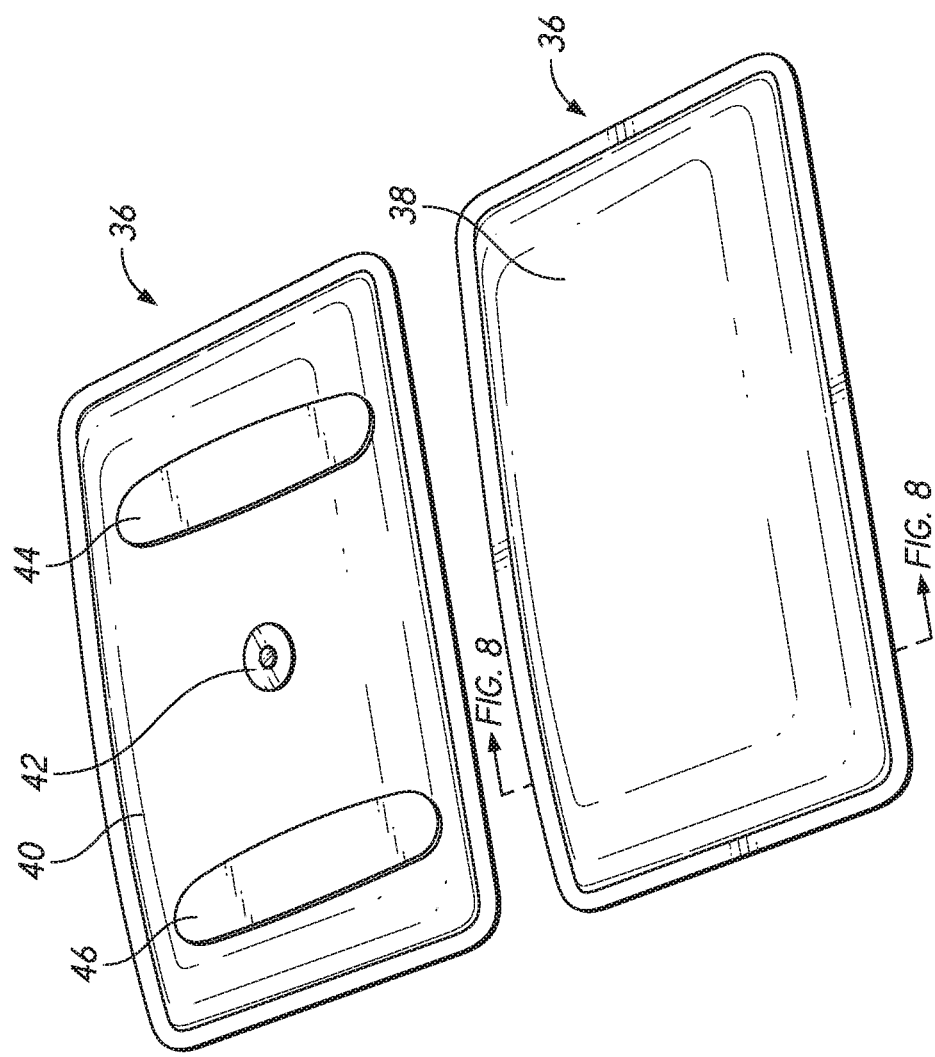
FIG. 7 is a perspective view, showing two exemplary thermal packs.

FIGS. 7-14 provide detail regarding some exemplary thermal packs. In reviewing these descriptions, the reader should bear in mind that the present invention is by no means limited to any particular type of thermal pack. FIG. 7 shows two examples of the same type of thermal pack 36. This example is a cold pack intended to receive heat transferred from a patient. The lower of the two thermal packs shown in FIG. 7 has inner layer 38 facing upward. This is the layer intended to press against the patient. It is covered in a smooth and comfortable material.

The upper of the two thermal packs shown in FIG. 7 is flipped over to expose outer layer 40. This outer layer will face away from the patient. It includes a pair of hook panels 44, 46. These hook panels are configured to secure the thermal pack in place when they are pressed against a panel having a loop covering. Expansion valve 42 selectively admits air when the thermal media within the thermal pack expands upon freezing (assuming that such a type of thermal media is used). At least a portion of outer layer 40 is preferably made transparent so that a user can see the contents of the thermal pack and observe whether the contents are liquid or frozen.

A heat transfer medium that undergoes a phase change offers advantages for the thermal packs 36. First, the use of a phase change allows the absorption of much more heat that would be possible in its absence. Second, the use of a phase change provides a steady temperature for the heat transfer medium as it is transitioning from a solid to a liquid (the temperature of a substance being constant in that process).

One suitable heat transfer medium is disclosed in U.S. Pat. No. 5,800,491 to Kolen and Nebolon. This patent discloses a composition of discrete hydrophilic absorbers that are hydrated with a liquid comprising a solution of water and a humectant selected from the group consisting of propylene glycol, ethylene glycol, glycerin, dimethyl sulfoxide, dimethyl formamide, and combinations thereof. The hydrophilic absorbers are discrete acrylic polymer granules, such as discrete cross-linked polyacrylamide copolymer granules. Upon freezing, this composition creates a solid state that is akin to packed snow or crushed ice. It remains pliable instead of freezing into a unified solid mass.

The interior of each thermal pack contains a heat transfer medium. This preferably includes the aforementioned hydrating liquid consisting of a solution of water and a humectant selected from the group consisting of propylene glycol, ethylene glycol, glycerin, dimethyl sulfoxide, dimethyl formamide, and combinations thereof (as described in the prior art section of this disclosure). Air is admitted to the interior through expansion valve 42 during the freezing process. When the medium melts, valve 42 allows air out of the enclosed interior but not the liquid medium.

Figure 8:
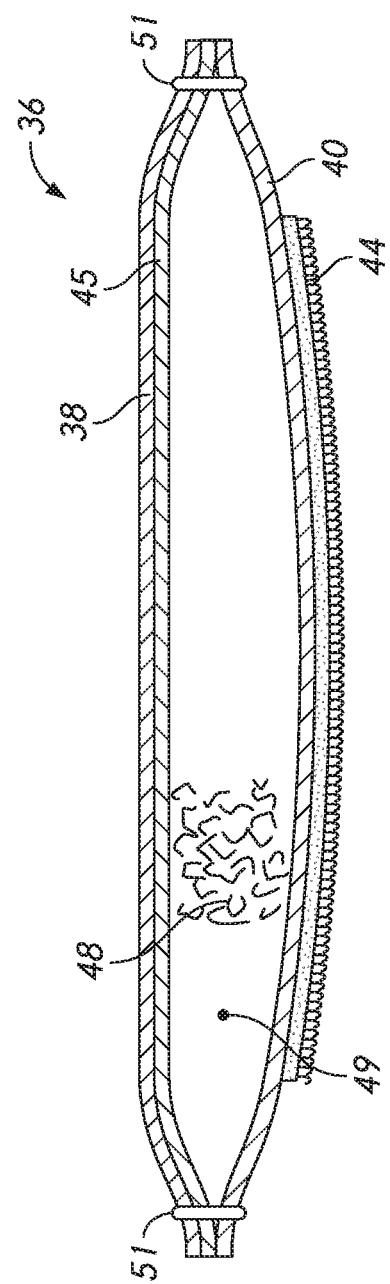
FIG. 8 is a sectional elevation view, showing internal details of a thermal pack.

FIG. 8 shows a section view through thermal pack 36. Two layers of sealing material—outer layer 40 and inner sealing layer 45 (the water impermeable layer) are heat staked together along sealed seam 51 (which runs along the entire perimeter of the thermal pack). The inward facing surface (the side intended to face the patient) also includes inner layer 38. This cover material is preferably a soft and compliant material that may be comfortably worn against the user's thin clothing (such as a T-shirt) or even directly against the user's skin. This material preferably wicks moisture away from the user. One of its main purposes is to serve as a barrier separating the user from direct contact with the thermal transfer pack. The material thereby regulates the rate of heat transfer to a desired level.

Inner layer 38 may be bonded to the thermal pack by any suitable method—including adhesives or stitching. It is preferable for the side facing the user to have no exposed discontinuities as these may be irritating. Bulk thermal media 48 is contained within interior volume 49 formed between the two layers of sealing material. Hook panel 44 is affixed to the outward-facing side of the assembly.

Figure 9:
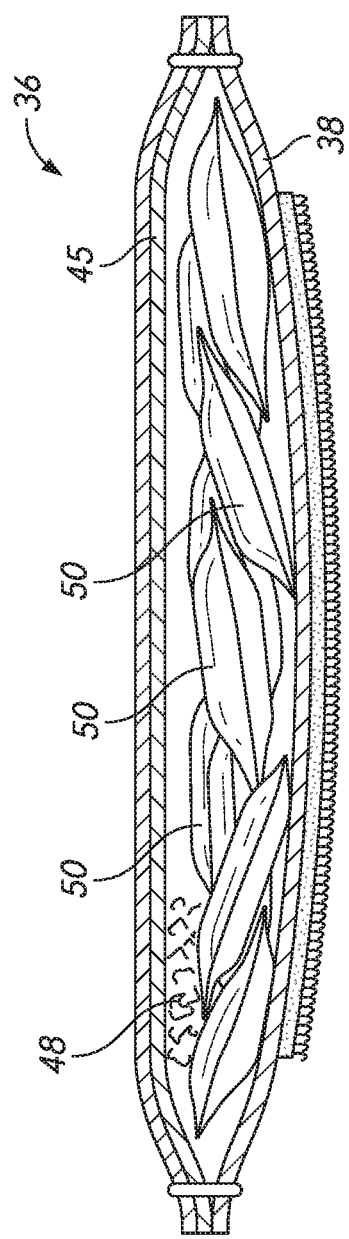
FIG. 9 is a sectional elevation view, showing internal details of an alternate embodiment of a thermal pack.

FIG. 9 shows an enhancement to the cooling pack shown in FIG. 8. Rather than placing the cooling media in a single compartment, the version of FIG. 9 places numerous small bags of cooling media into a larger bag. Sub-bags 50 are relatively small—on the order of 0.5 to 2 inches square (1.25 cm to 5.0 cm). In many instances it will be preferable to make them even smaller—such as 0.2 inches square (0.5 cm). The most preferred size is 0.75 inches square (1.25 cm square).

As explained previously, the cooling media contained within the interior is preferably a substance such as shown in U.S. Pat. No. 5,800,491 to Kolen and Nebolon. This substance forms an organized crystalline solid with a consistency similar to snow. Even as a solid, it remains soft and malleable. However, the substance such as disclosed in the '491 patent does not absorb as much energy during the transition from a solid to a liquid as pure water. Water can absorb more thermal energy, yet water has an undesirable property in that it solidifies into a hard mass (ice). If the entire volume within the thermal pack were simply filled with water and frozen, the result would be a rigid object that would be quite uncomfortable to the patient.

The thermal pack of FIG. 9 provides the advantageous latent heat of water while retaining most of the beneficial aspects of the substance described in the '491 patent. Each sub-bag 50 is filled with water. Small amounts of other substances may be present as well, but water is by far the main constituent. The volume contained within the interior of the thermal pack but outside sub-bags 50 is filled with a substance that creates a snow-like solid (such as described in the '491 patent). The result is an advantageous combination of features. Each individual sub-bag 50 freezes into a hard object (containing ice). The surrounding volume freezes into a malleable snow-like substance. The sub-bags are relatively small—preferably less than 3 cm on a side. Thus, the overall thermal pack 36 can still bend and flex because the sub-bags 50 can move about within the snow-like frozen substance surrounding them. The user employs the thermal pack of FIG. 9 in the same way as the thermal pack of FIG. 8. However, the composite nature of the bag allows a greater absorption of thermal energy for the same unit volume.

In some versions of the composite thermal transfer pack the sub-bags or outer bag can include a thermochromatic material. This material changes color when the media freezes—thereby clearly indicating to the user whether all the sub-bags are fully transitioned to a solid. In some versions a thermochromatic ink may be added to the water within sub-bags 50. In other versions, the thermochromatic material will be a film added to the sub-bags, the overall bag, or both.

Figure 10:
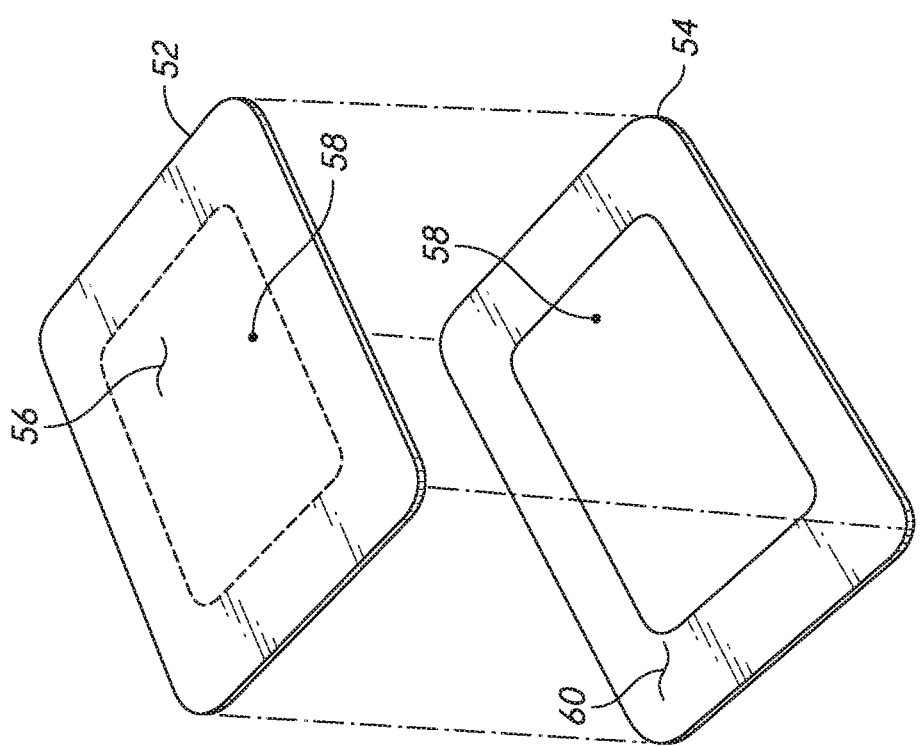
FIG. 10 is an exploded perspective view, showing a sub-bag used in one of the thermal packs.

FIGS. 10-14 show a preferred embodiment employing thermochromic materials to indicate when the water in the sub-bags is frozen. FIG. 10 depicts an individual sub-bag in a disassembled state. First panel 52 is configured to join second panel 54 by joining the perimeter of the two panels together to form a continuous seal (such as by heat fusing or ultrasonic welding)

Figure 11:
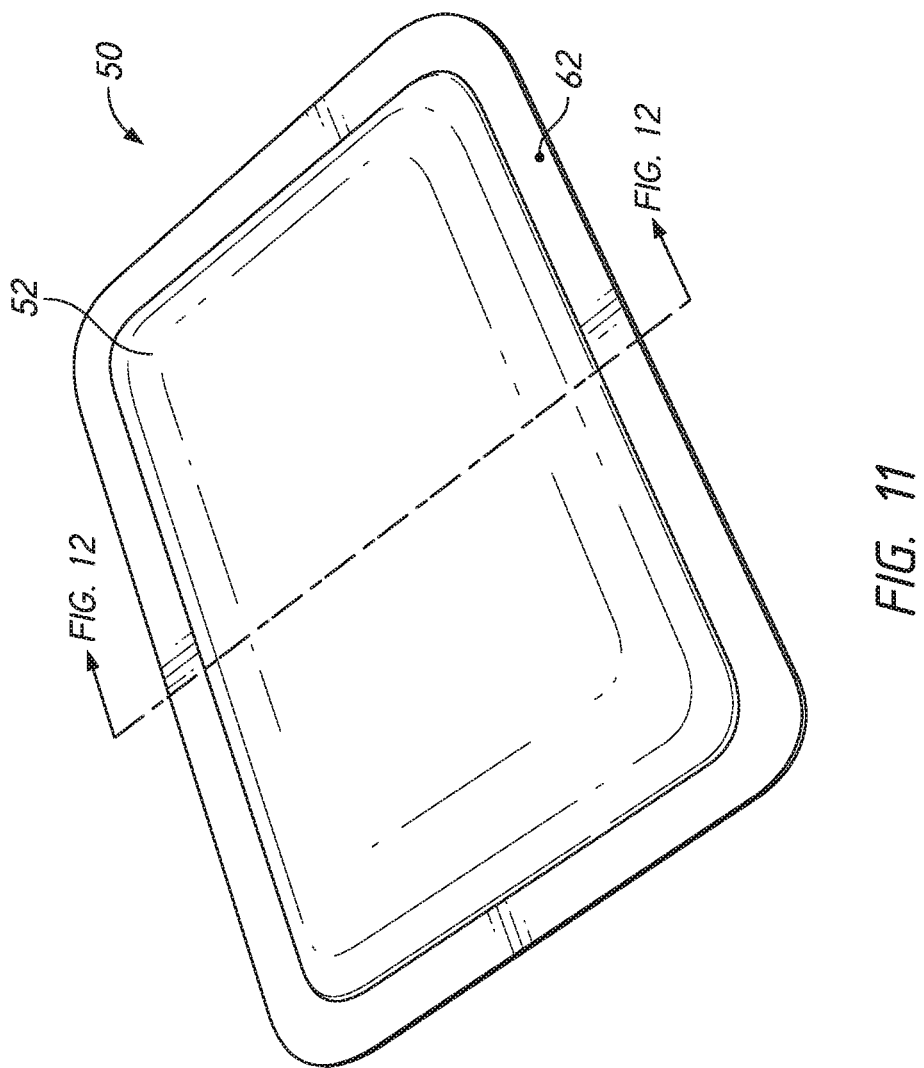
FIG. 11 is a perspective view, showing a sub-bag

FIG. 11 shows the two panels joined together to form sub bag 50. The bag is filled with water. Sealed perimeter 62 is formed around the perimeter of the two panels so that the water cannot escape.

The present invention is by no means limited to any particular method for making the sub bags, and in fact the sub bags may be made using many different methods and materials. One approach is to fold a single piece of flexible material over on itself. One "sealed edge" is created by the fold and the remaining three edges may then be sealed using a suitable method. Another approach is to cut lengths from a continuous tube of flexible material (possibly stored on a roll). The two cut ends can then be sealed using a suitable method.

The operation of sub bag 50 is quite simple. When the sub bag is exposed to temperatures below 0 degrees centigrade for a sufficient period the water within the bag freezes. As is widely known, water displays the unusual characteristic of expanding as it transitions from a liquid to a solid. The material used for the panels 52, 54 is preferably sufficiently elastic to accommodate many freezing and thawing cycles without breaking down. Another option is the inclusion of an air pocket within the sub bag so that the volumetric change is accommodated by varying air pressure. Yet another option is including some type of air valve. However, it is preferable to maximize the heat transfer to and from the bag and to minimize complexity. Thus, the preferred embodiments contain plain water and do not incorporate any sort of valve. The term "plain water" shall mean pure water and solutions in which water makes up 95 percent of the total solution by mass. In some embodiments a small amount of other material may be added to the water to adjust the freezing point, to inhibit growth of organic materials, or for some other purpose. However, the other material shall not exceed 5% of the total solution by mass.

Returning to FIG. 10, the reader will note that the two panels 52, 54 each have an outer surface 56 and an inner surface 60 (referring to the inner and outer surfaces that will result once the two panels are joined together). Each of the two panels 52, 54 also has an indicating area 58. The indicating area may be located on an inner surface, an outer surface, or both (and may in fact comprise the entire surface). However, in the embodiment shown, indicating area 58 is located on the inner surface of each panel.

Indicating area 58 preferably includes a thermochromic material applied to the surface of the panel. The thermochromic material preferably changes color at a set point that indicates a complete freezing of the water within the bag. As an example, the set point might be −2 degrees centigrade. At this point, the thermochromic material can be configured to change from clear to opaque (such as a medium blue color). When a user sees this color, it indicates that the contents of the particular sub bag have completely frozen. Certain other thermochromic materials may change from one color to another color (such as white to indigo).

A thorough discussion of thermochromic materials is beyond the scope of this disclosure. However, an exemplary choice is a leuco dye secured in microcapsules. Commonly used leuco dyes include sprirolactones, fluorans, spiropyrans, and fulgides. The microcapsule containing the dye is a small enclosed volume that retains the dye without leakage. The encapsulating material is thermally conductive so that the surrounding temperature is quickly assumed by the leuco dye within the microcapsule. Because the mass of leuco dye within each microcapsule is very small, it can change temperature rapidly. These microcapsules can be adhered to the inner surfaces of the panels 52, 54. A sufficiently dense array of such microcapsules will be in contact with the water within the sub bag.

Those skilled in the art will know that leuco dye microcapsules can be printed on a surface or sprayed on a surface. They may even be embedded in the material itself as it is manufactured. Leuco dyes are known to have limited accuracy in their indication, since the color change usually occurs in about a 3 degree centigrade band. With this in mind, one could select a leuco dye that transitioned to the opaque state between −1 and −4 degrees centigrade. With such a selection, the dye would reliably indicate the frozen state.

Those skilled in the art will also know that liquid crystal thermochromic agents generally have a better temperature accuracy than leuco dyes. One could employ liquid crystal materials though this would likely drive up the cost and limit the color choices. The present invention is by no means limited to any particular thermochromic agent, nor is it limited to any particular method of applying the thermochromic agent.

As an example, one may consider an embodiment where the sub-bags are made from a long length of flexible tube. The tube may be cut at suitable intervals to create a short, tubular section with two open ends. The two open ends are sealed to form the sub-bag. In this example the leuco dye may be a printed continuously along the entire inward-facing surface of the flexible tube. The result is that the inward-facing surface of the sub-bag is covered by the leuco dye. From the user's perspective, the entire sub-bag will appear to include the leuco dye. Thus, the color change will appear to be the entire sub-bag.

Figure 12:
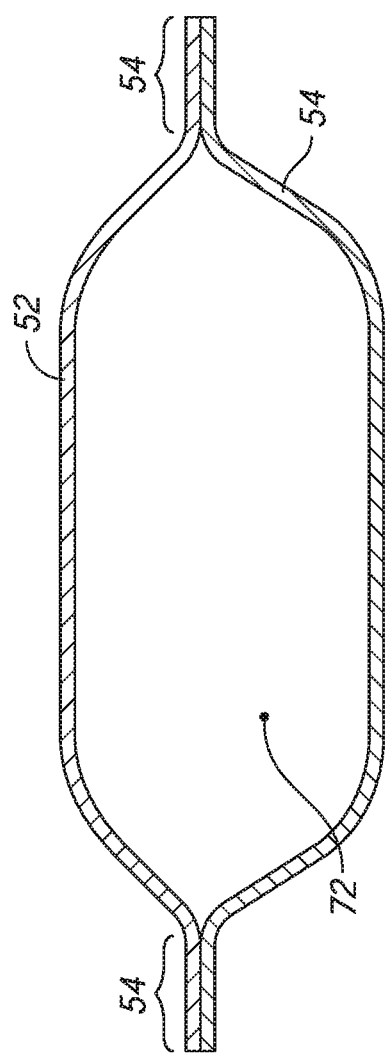
FIG. 12 is a sectional elevation view, showing internal details of a sub-bag.

FIG. 11 provides a perspective view of sub bag 50 filled with water. FIG. 12 provides a sectional elevation view through the bag depicted in FIG. 11. A volume of water 72 is trapped between the panels 52, 54 and contained by sealed perimeter 62. The thermochromic agent is preferably placed on the inner surface of each panel so that it has more direct contact with the water.

Figure 13:
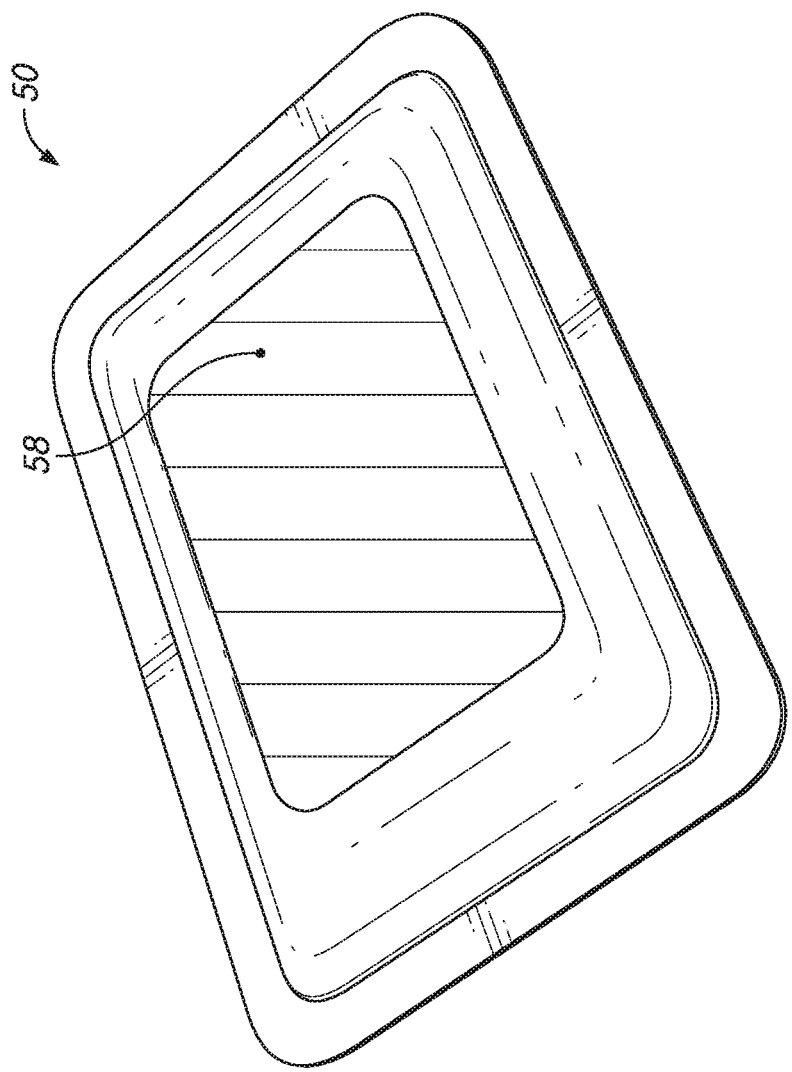
FIG. 13 is a perspective view, showing the addition of a temperature indicating area to a sub-bag.

FIG. 13 shows a perspective view of the same sub bag 50 after the thermochromic material has transitioned to an opaque state. The material selected for panels 52, 54 should be transparent or semi-transparent if the thermochromic material is placed on the inner surface of the panels. In the example of FIG. 13 the material of the panels is transparent and the thermochroic material is deposited on the inner surface of the panels. Indicating area 58 is visible from the exterior of the sub bag as shown. The indicating area is depicted as a cross-hatched area. In reality, the indicating area will appear as an opaque region. For example, if a medium blue thermochromic agent is used, then indicating area 58 will appear as a blue rectangle on the panels (and the user will likely not perceive the fact that the thermochromic agent is on the inner surface but will instead just perceive the appearance of a blue rectangle on the visible outer surface).

Figure 14:
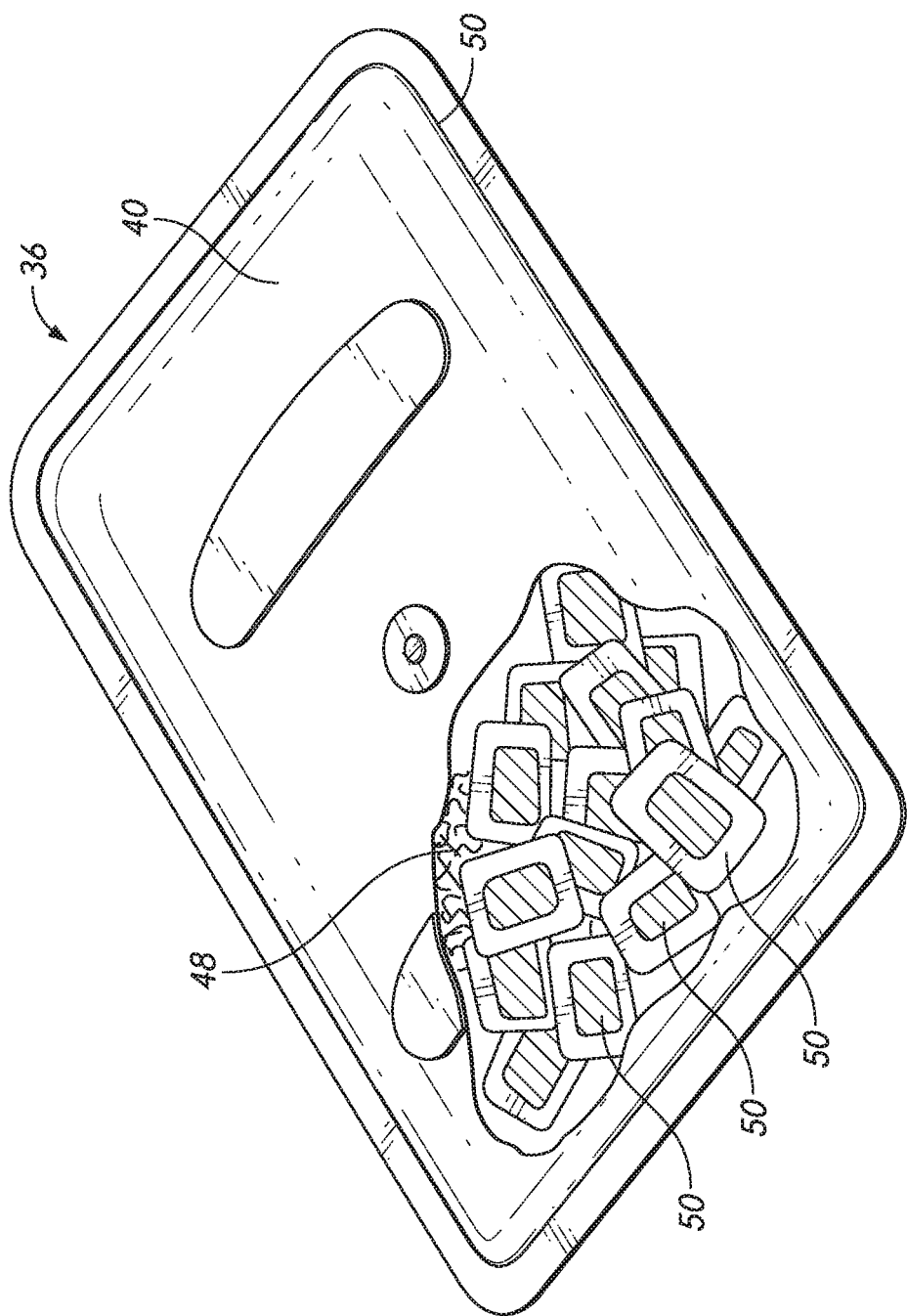
FIG. 14 is a perspective view with a cutaway, showing the use of bulk thermal media and a plurality of sub-bags in a thermal pack.

As explained previously, the inventive thermal transfer pack places a plurality of sub bags 50 into a larger bag. FIG. 14 shows a thermal pack 36 made by placing a number of sub bags 50 and surrounding bulk thermal media 48 into a sealed bag. A cutaway is included in the view to clearly show sub bags 50.

The sub bags are surrounded by the bulk transfer media that freezes into a highly crystalline structure akin to snow. Upon freezing, this duplex composition creates a solid state that remains pliable instead of freezing into a unified solid mass. The composition has been previously referred to as a "heat transfer medium." In the context of the inventive duplex thermal transfer pack the use of the term "heat transfer medium" is a bit vague, since both the water and the mixture of hydrophilic absorbers and water with a humectant as a "heat transfer medium." Accordingly, the water and humectant solution shall be referred to as a solid-pliable heat transfer medium in the context of the duplex thermal transfer pack. A solid-pliable heat transfer medium is one which remains pliable after the water it has contained transitions from a liquid to a solid.

The sealing material that is used in the creation of outer layer 40 preferably has a transparent surface that allows the user to see the condition of the sub bags within. A user typically places thermal pack 36 in a freezer for a long enough period to convert the heat transfer medium to a crystalline solid and to freeze the water within the sub bags 50. The user can visually confirm the freezing of the water in the sub bags by noting the change of color on the indicating areas on the sub bags (the areas containing the thermochromic material). The transparent surface should be sufficiently clear to allow a user to perceive the color change of the sub bags that are pressed up against the other side of the surface. A thin and clear plastic material is sufficient.

The transparent surface may only extend for part of one side of the bag, or it may extend for more than that. In the example of FIG. 14, portions of transparent surface are covered by the hook panels. Other portions of the transparent surface may be covered by the expansion valve.

Most of the volume within thermal pack 36 is consumed by the sub bags 50. Each sub bag is relatively small compared to the thermal transfer pack as a whole, however. Preferably, the longest dimension of a sub bag is less than ⅓ of the longest dimension of the thermal pack as a whole. Even more preferably the longest dimension of a sub bag is less than ¹/₁₀ of the longest dimension of the thermal pack as a whole.

As an example, the thermal transfer pack of FIG. 14 has a longest dimension of 28 cm. A sub bag 50 used in this example might have a longest dimension of 2.5 cm. The sub bags are preferably pillow-shaped. In this example, the sub bag dimension are 1.25 cm×2.5 cm×0.50 cm. When the thermal transfer pack is placed in the freezer, the sub bags freeze into hard little "plates." The surrounding solution of water and a humectant freezes into a crystalline structure resembling packed snow. It remains soft and malleable. Because the now-hard sub bags are small in comparison to the overall volume of the thermal transfer pack—and because the interstices between the sub bags are packed with the soft "snow"—the thermal transfer pack as a whole retains a soft and malleable feel.

Figure 15:
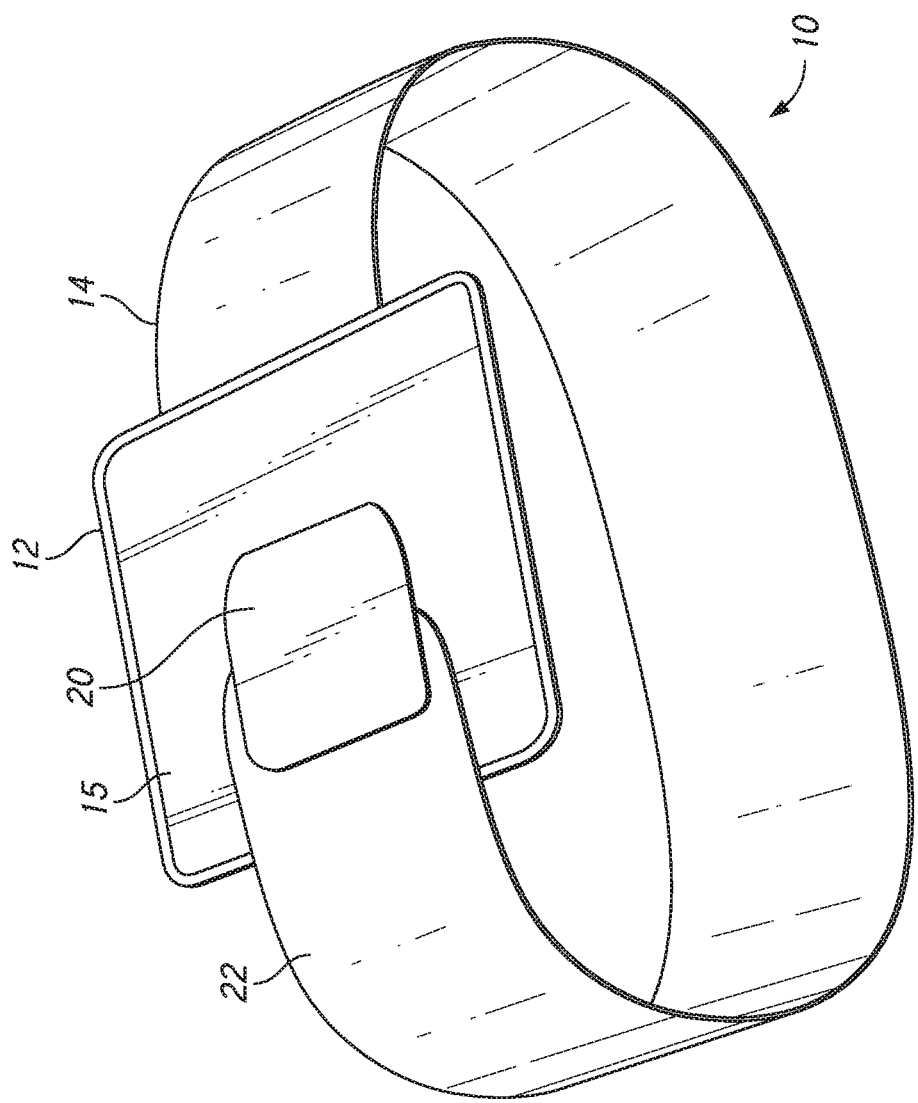
FIG. 15 is a perspective view, showing one assembled state for the inventive wrap.
Figure 16:
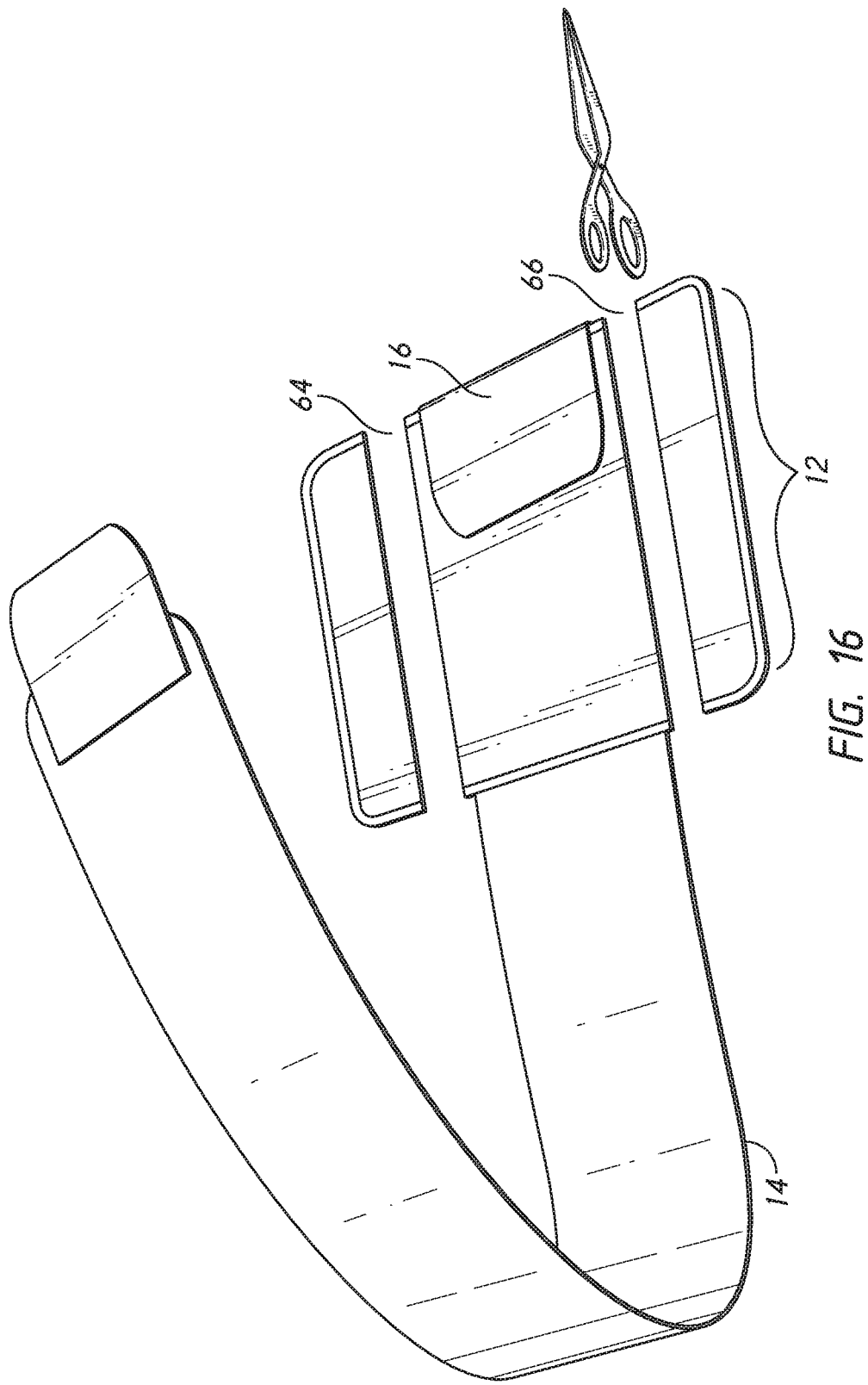
FIG. 16 is a perspective view, showing how the width of the body of the wrap can be modified.
Figure 17:
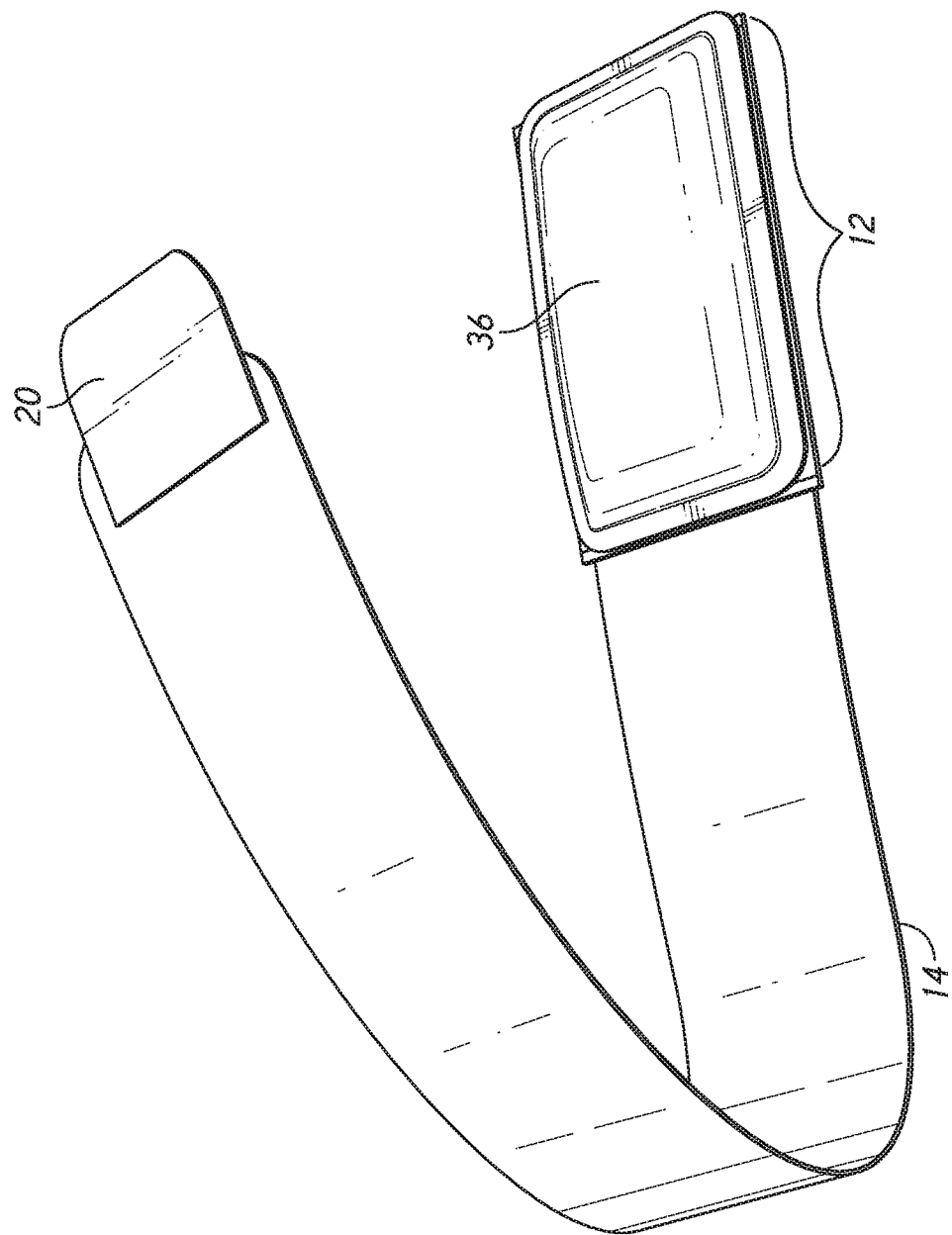
FIG. 17 is a perspective view, showing the embodiment of FIG. 16 with the addition of a thermal pack.

FIGS. 15-17 illustrate exemplary configurations for the universal wrap. In FIG. 15, outer surface 15 of body 12 is facing toward the user. Strap 14 is in an uncut state. It is formed into a loop as shown. Hook panel 20 has been used to secure the strap to outer surface 15 by pressing the exposed portion of the hook surface on the hook panel into outer surface 15 of body 12. An encircling loop is thereby formed. This loop can be placed around the patient's waist or chest in order to press thermal packs affixed to body 12 (on the side facing away from the viewer) against the patient. The outer surface of strap 14 and body 12 are provided with a loop covering. Thus, the overall circumference can be adjusted by adjusting the overlap of the strap and securing hook panel 20 to a desired position on the body or the strap.

FIG. 6 shows a configuration where the strap has been cut in two and the two segments are then joined on the side of the loop opposite to body 12. This configuration has been described previously and will not be repeated here.

FIGS. 16 and 17 illustrate still another configuration—in which the size of body 12 is reduced. Body 12 is preferably made of a fabric that can be cut to produce a clean and stable edge. Cuts 64, 66 have been made in FIG. 16 to match the width of body 12 to that of strap 14. Turning to FIG. 17, a single rectangular thermal pack 36 has been affixed to the modified body 12. This configuration provides a smaller contact area that is suitable for some applications.

Returning to FIG. 16, it is also possible to make a single cut that is perpendicular to the orientation of the cuts shown. This single cut would remove the region of tab 16, resulting in a "T" shape with the strap being the long part of the T and the remaining shape of the body being the cross piece. This configuration is a good shape for use on the back of a patient's elbow. Of course, the practitioner is not limited to perpendicular cuts. In some instances an angled or curved cut will be advantageous and these are available as well.

Figure 18:
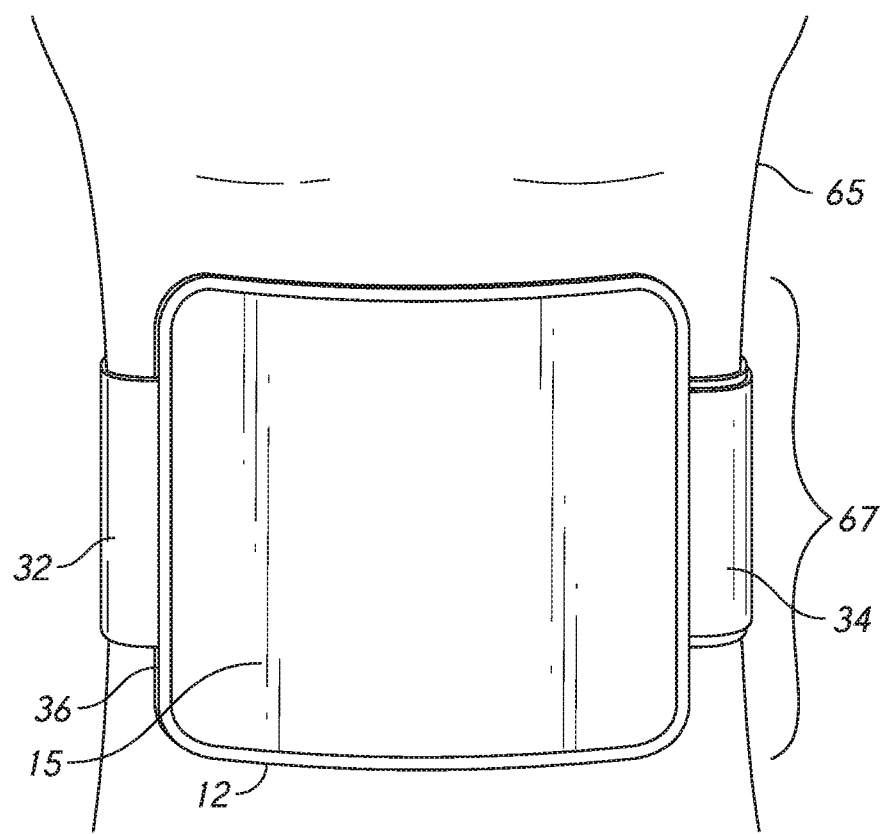
FIG. 18 is a perspective view, showing the inventive wrap applied to a lumbar region of a patient.

FIGS. 18-27 illustrate examples of how the universal wrap can be applied to a patient. FIG. 18 shows the example of a patient needing cold therapy for the lumbar region. The goal is to place thermal packs affixed to body 12 over lumbar region 67. This example starts with the configuration of FIG. 6. One or more thermal packs are affixed to inner surface 18 of body 12 as shown.

The assembly is then lifted into position with the thermal packs pressed against the patient's lumbar region as shown in FIG. 18. First segment 32 is pulled around the left side of the patient's waist and second segment 34 is pulled around the right side of the patient's waist. Looking now at FIG. 19, the patient adjusts the amount of pressure by stretching the first and second segments. When the pressure is at the desired level, she secures the first and second segments into a belt by pressing hook panel 20 into the loop covering on first segment 32.

Figure 19:
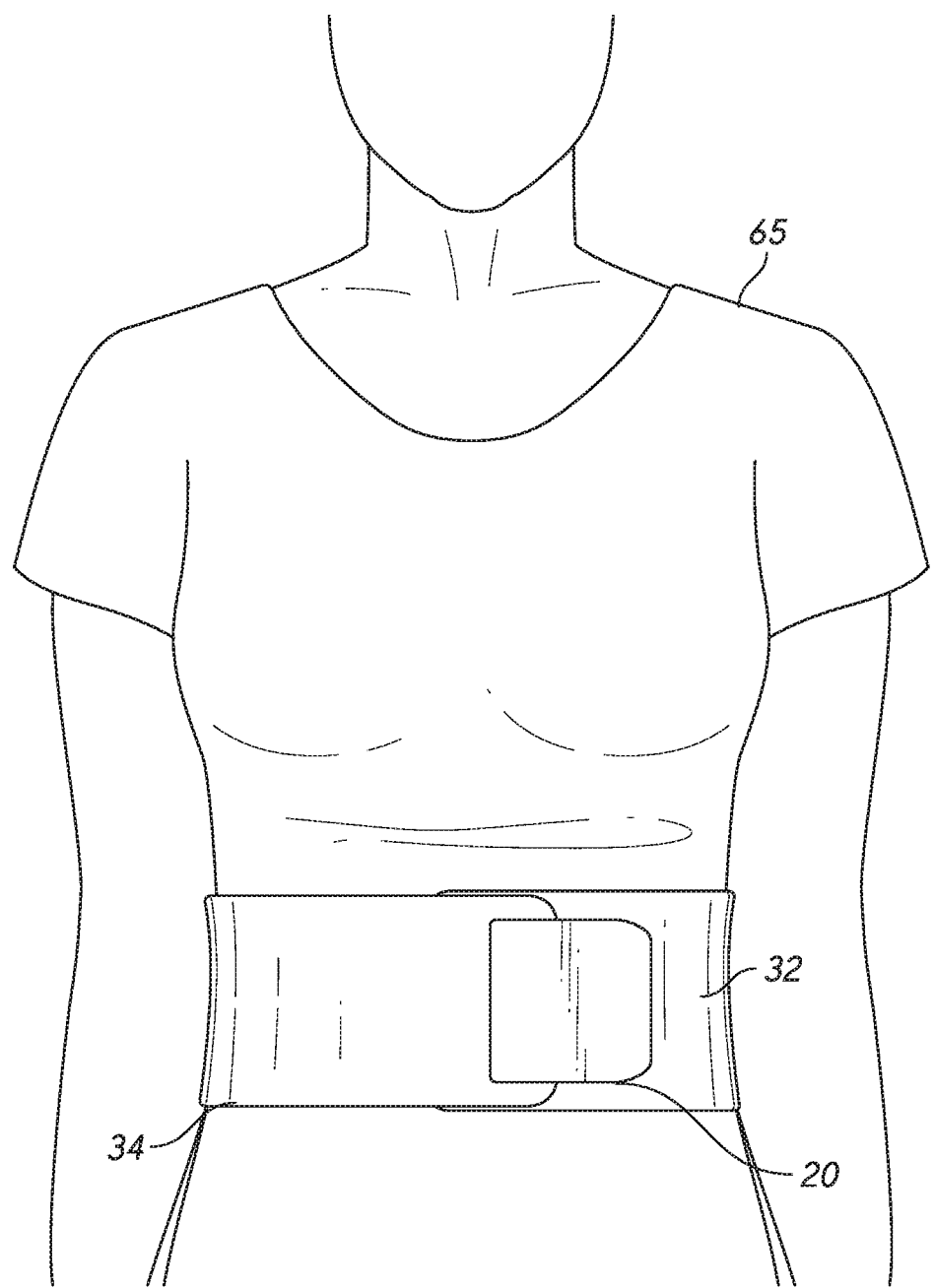
FIG. 19 is a perspective view, showing the configuration of FIG. 18 from an anterior vantage point.

For a patient having a waist size as depicted in FIG. 19, it will often be advisable to cut a segment off the distal end of first segment 32, second segment 34, or both. These cuts can be made to place hook panel 20 in a convenient location. This is desirable because the user will periodically remove and reinstall the wrap assembly (or a healthcare provider will do so). If the thermal packs are cold packs as shown in FIG. 9, they will need to be replaced approximately every four hours. In order to replace the packs the user will typically remove the wrap, peel the old packs off of body 12, and stick on new packs that have just been removed from a freezer. The old packs will then be placed in a freezer. In some applications the packs can be removed by folding down a portion of body 12 while leaving the wrap in place. This is an optional method.

Figure 20:
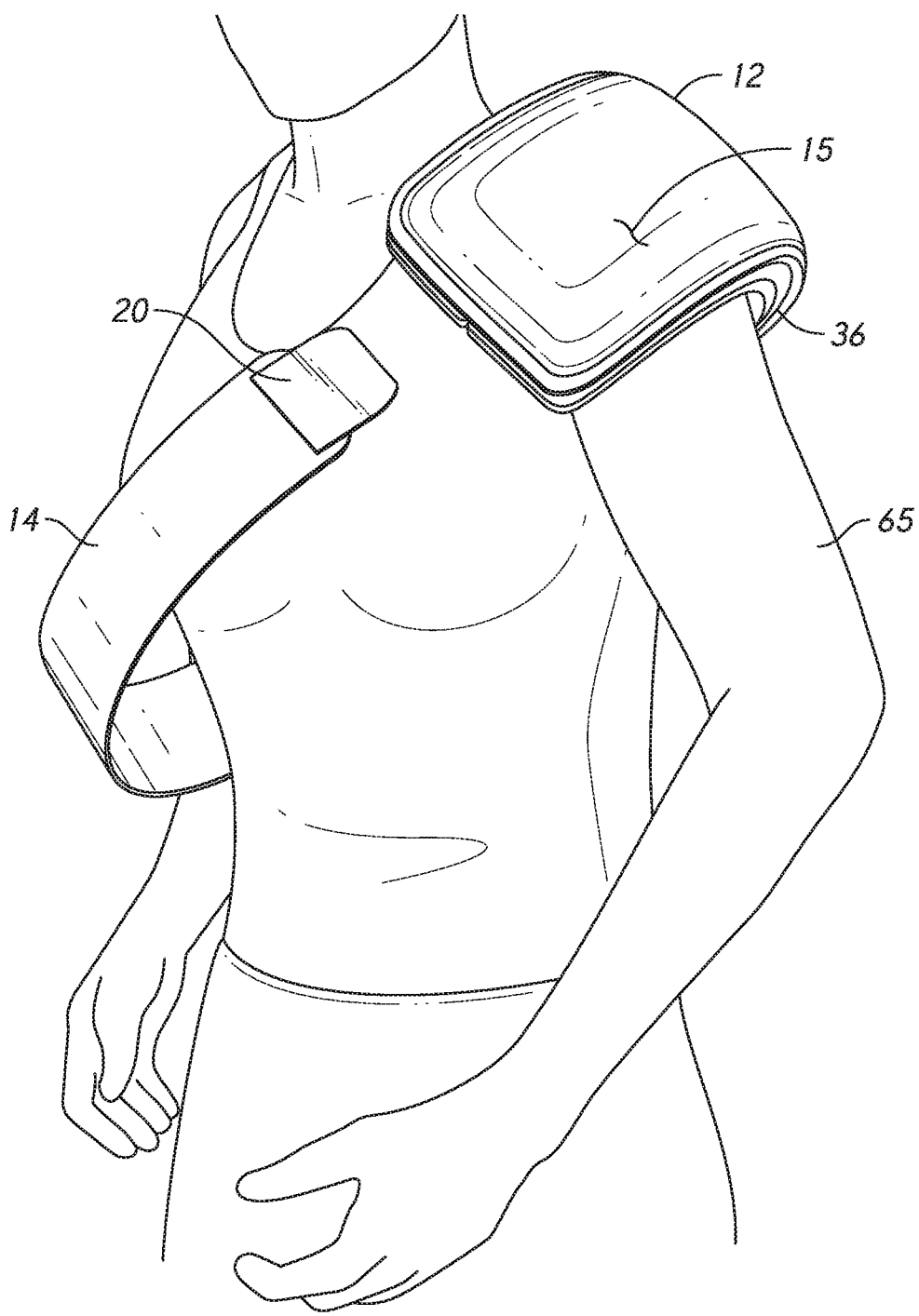
FIG. 20 is a perspective view, showing the inventive wrap applied to a shoulder of a patient.
Figure 21:
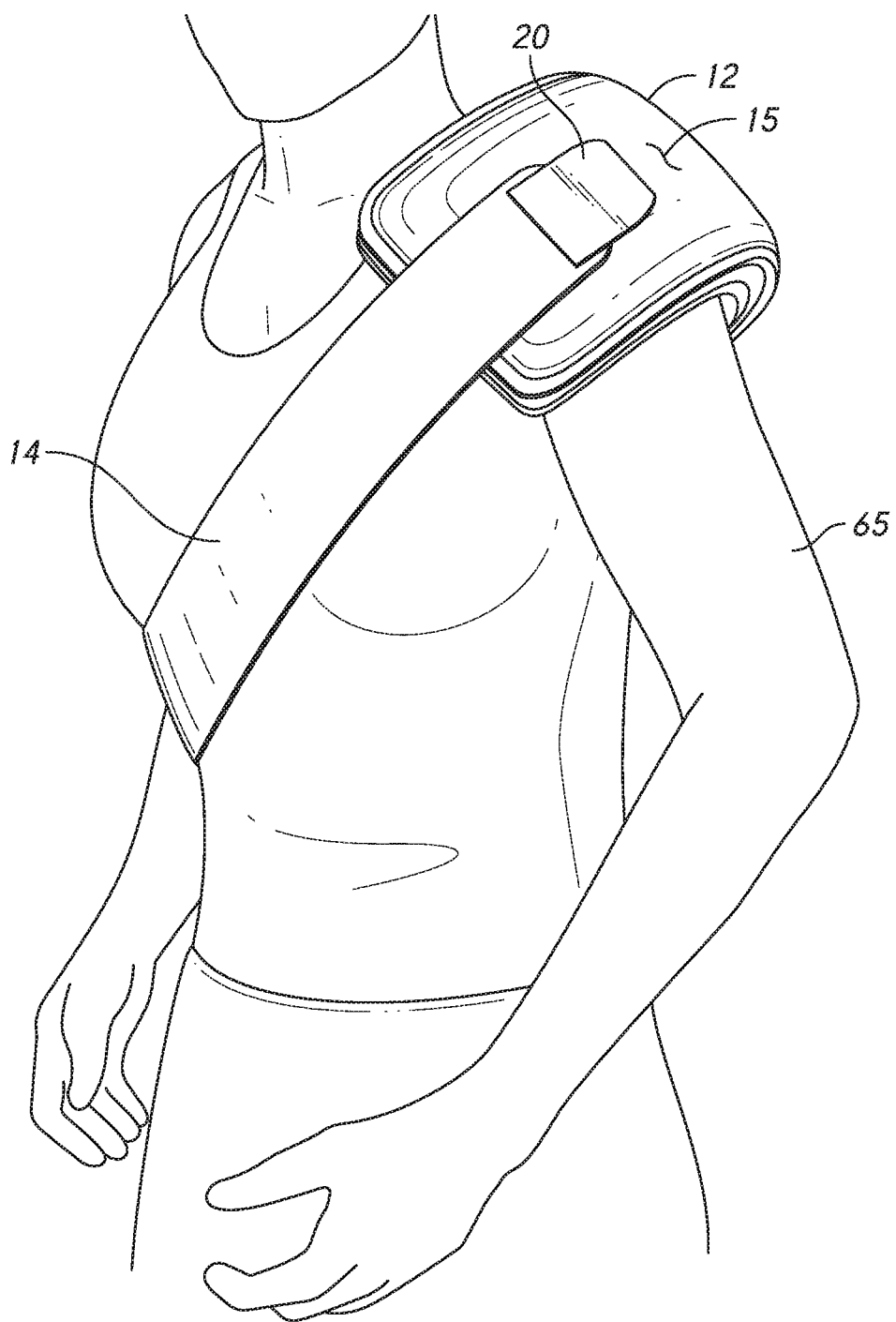
FIG. 21 is a perspective view, showing the inventive wrap applied to a shoulder of a patient.

FIGS. 20 and 21 show a first approach to placing the universal wrap on a patient's shoulder. A pair of thermal packs are affixed to body 12 and the assembly is then placed on the left shoulder of patient 65. Strap 14 is passed around her back and brought through the gap between her torso and her right arm. The strap is tightened to a desired extent and then hook panel 20 is secured to the loop covering on outer surface 15. The tension on the strap urges the thermal packs beneath body 12 against the patient's shoulder.

FIG. 21 shows the secured configuration with hook panel 20 secured to outer surface 15. This configuration can be difficult to remove for some patients. The left arm is likely immobile, since an injury to the left shoulder is being treated. The patient must therefore pull hook panel 20 free by crossing her right arm over her body and using her right hand to grasp the hook panel. In patients with limited mobility this motion can be difficult.

Figure 22:
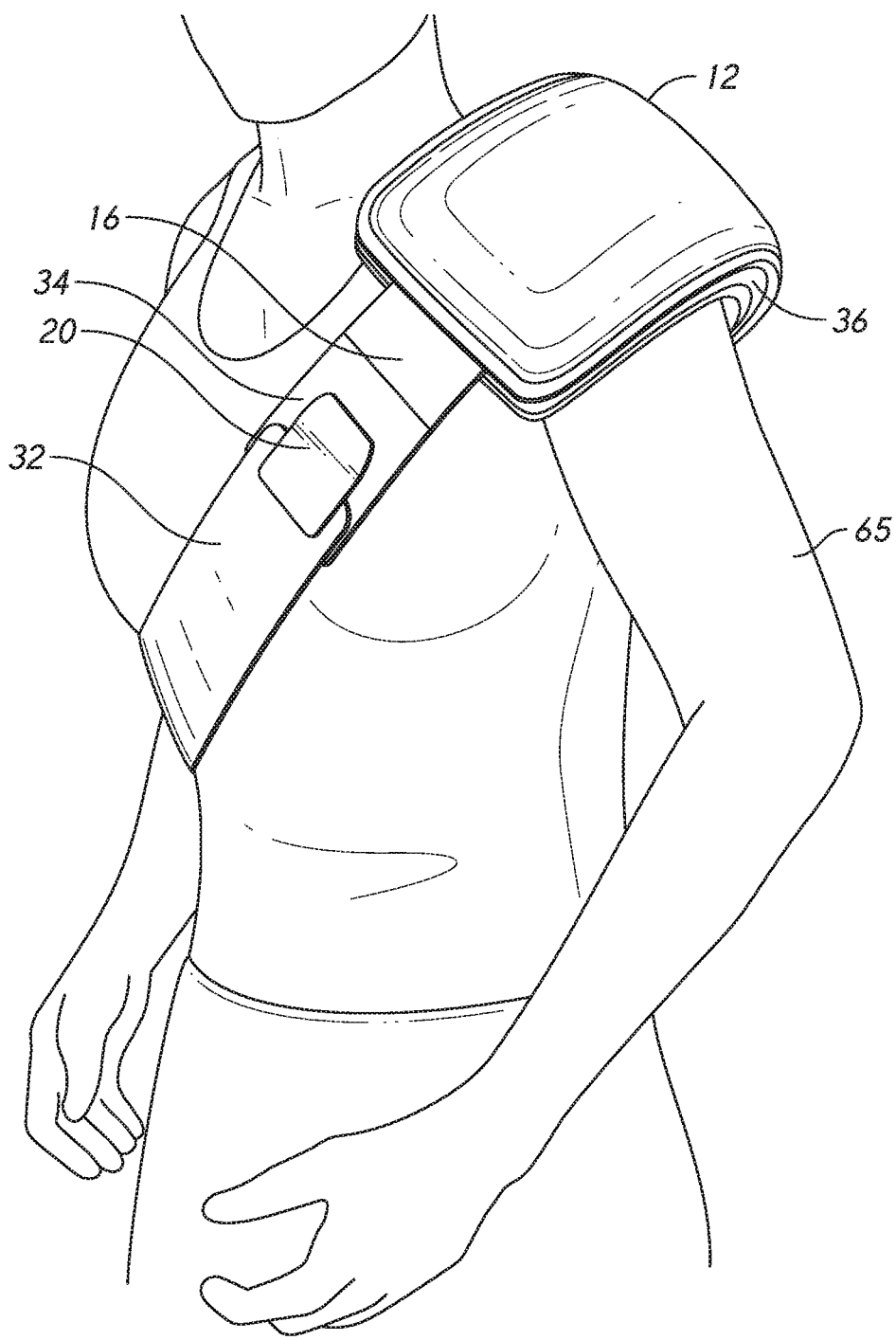
FIG. 22 is a perspective view, showing the inventive wrap applied to a shoulder of a patient.

FIG. 22 shows an alternate method of using the universal wrap to place a thermal pack on a shoulder. This version starts with the configuration of FIG. 4, except that cut 30 is made much further away from body 12 so that second segment 34 is quite short. Returning now to FIG. 22, tab 16 is pulled out from body 12 and second segment 34 is secured to tab 16 by pressing the second segment against the hook surface on the tab. First segment 32 is pulled around the patient's body and through the gap between her torso and her right arm. Hook panel is transferred to the distal end of first segment 32 as shown. The loop is then formed by securing hook panel 20 to the distal end of first segment 32 and pressing the free end of the hook panel into second segment 34. The advantage of this configuration is the fact that hook panel 20 is much easier for the user to reach with her right hand.

Figure 23:
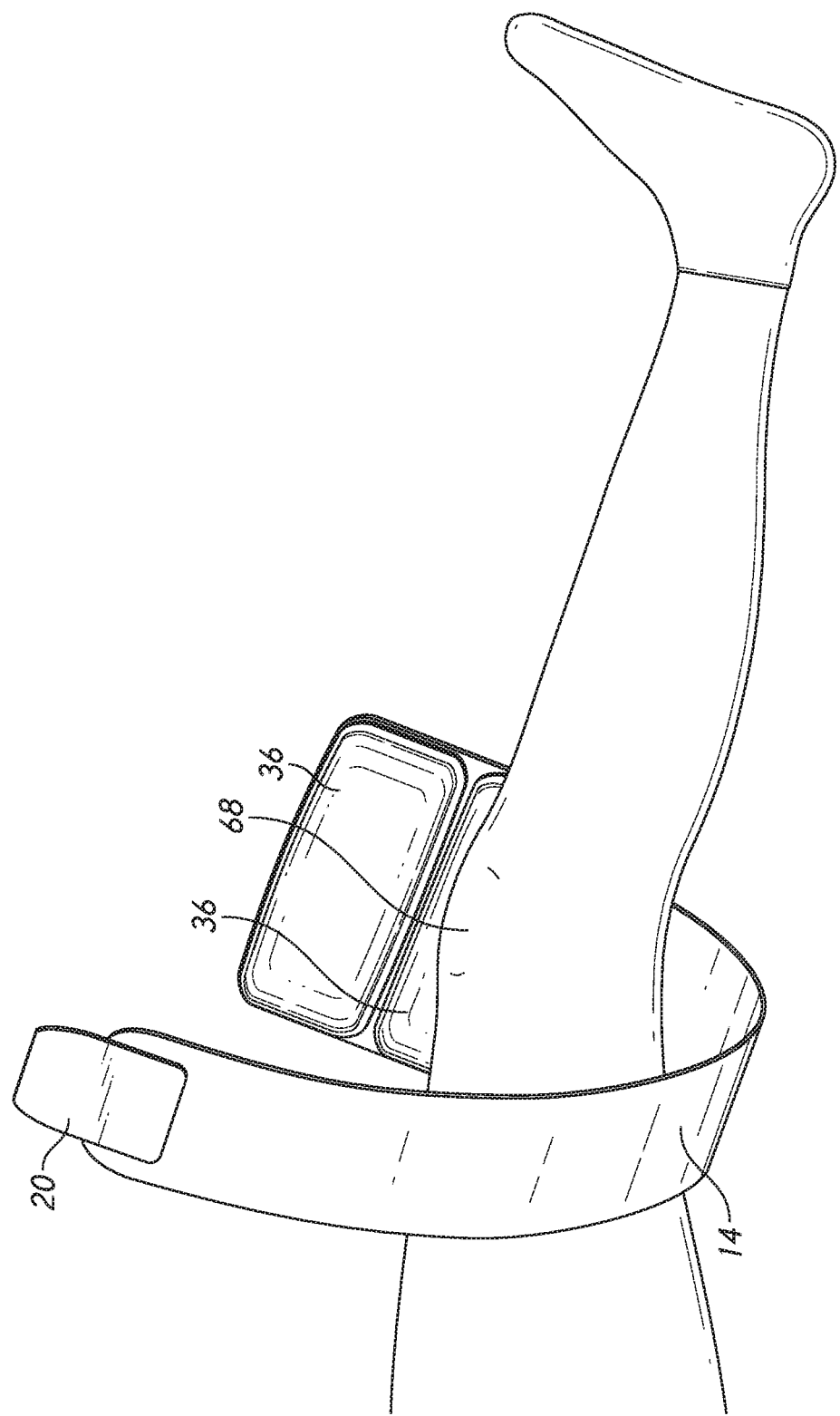
FIG. 23 is a perspective view, showing the inventive wrap applied to a knee of a patient.
Figure 24:
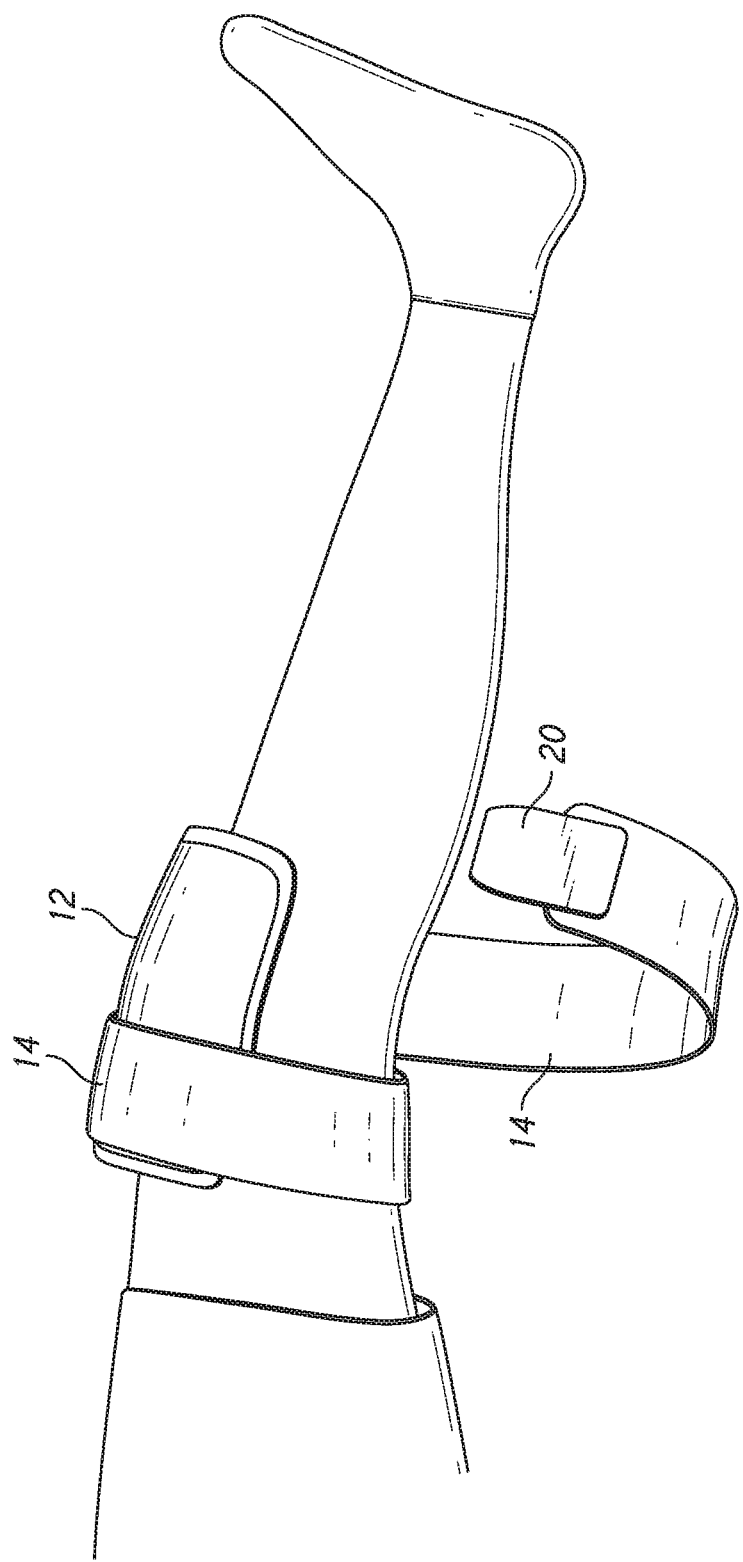
FIG. 24 is a perspective view, showing the inventive wrap applied to a knee of a patient.
Figure 25:
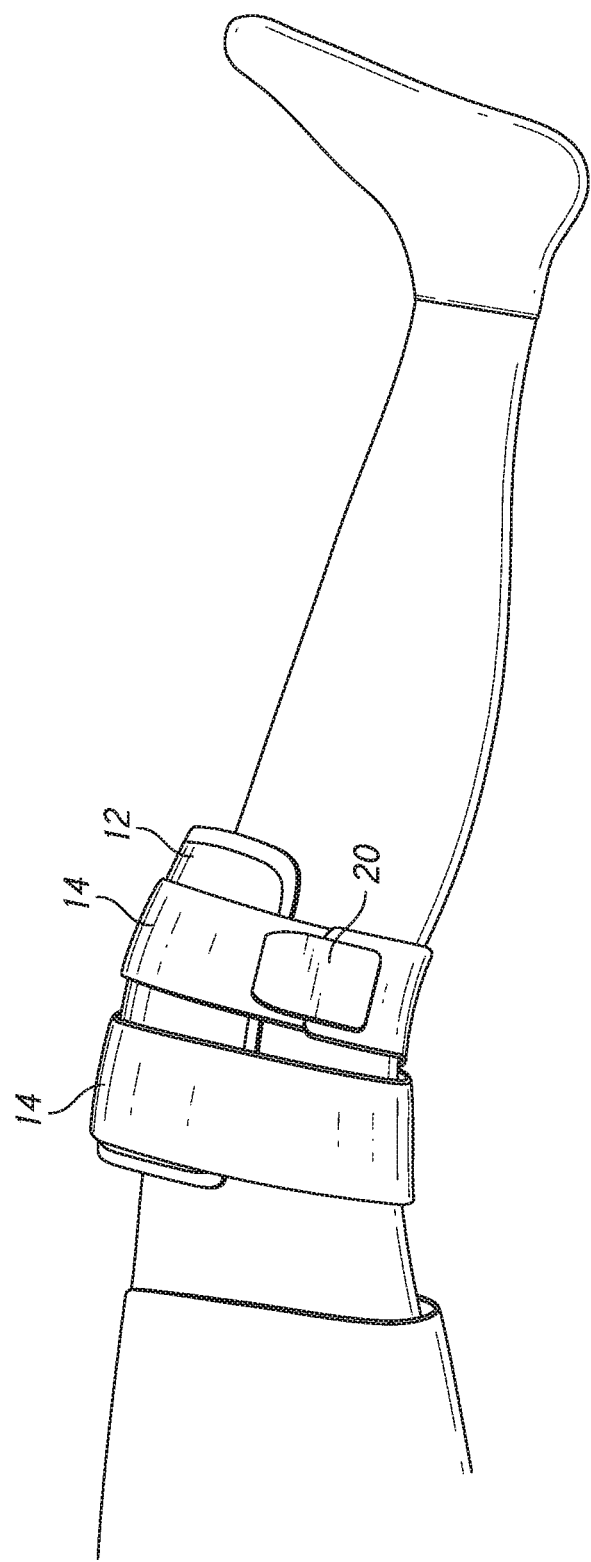
FIG. 25 is a perspective view, showing the inventive wrap applied to a knee of a patient.

FIGS. 23-25 show a method of applying the inventive universal wrap to a patient's knee. This process starts with the configuration of FIG. 1. A pair of thermal packs 36 are affixed to the inner surface of body 12. Strap 14 is passed around the area of knee 68—as shown. Hook panel 20 is placed on the distal end of the strap.

The reader will recall that strap 14 is preferably elastic. In the knee application, the strap can be stretched in a fashion similar to an ACE bandage in order to create a compressive wrap. FIG. 24 shows the process after strap 14 has been stretched and wrapped around the lower thigh. The distal end of the strap is then wrapped around the inferior knee region. FIG. 25 shows the final result. The strap is wrapped nearly three times around the knee and secured in place by pressing the exposed portion of hook panel 20 back against the outer surface of the strap itself. Tension on the strap urges the thermal packs beneath body 12 against the knee.

Figure 26:
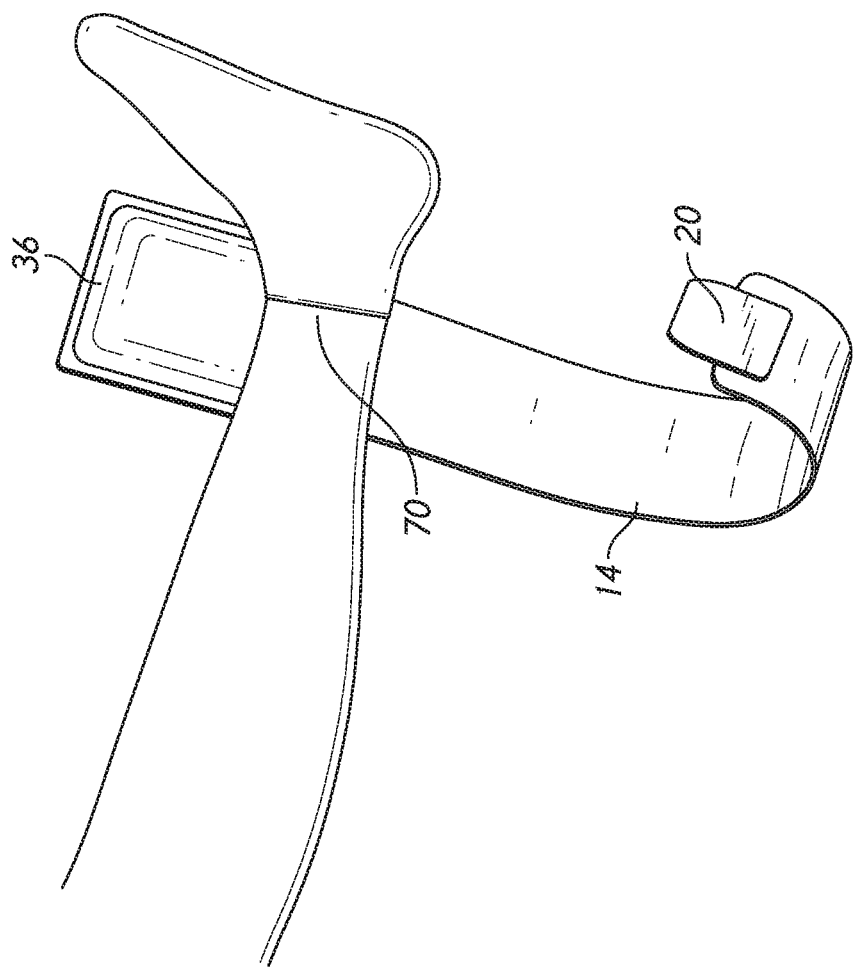
FIG. 26 is a perspective view, showing the inventive wrap applied to an ankle of a patient.
Figure 27:
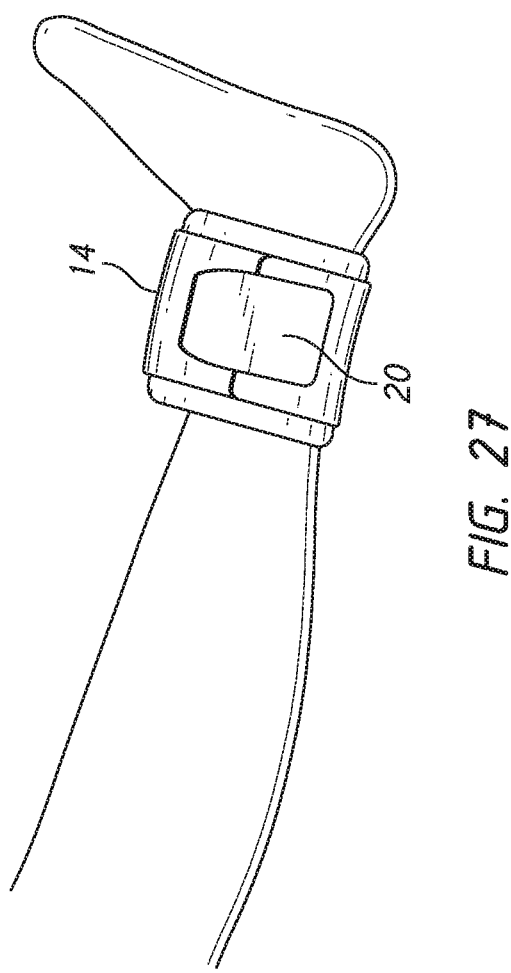
FIG. 27 is a perspective view, showing the inventive wrap applied to an ankle of a patient.

FIGS. 26 and 27 show an example of applying the inventive universal wrap to a patient's ankle. This process starts with the configuration of FIG. 17. FIG. 17 shows a single thermal pack 36 affixed to a body 12 that has been reduced in size. Turning to FIG. 26, thermal pack 26 is placed over the anterior portion of the patient's ankle. Strap 14 is passed around the ankle with hook panel 20 affixed to its distal end. The strap is then stretched and wrapped around the ankle one or more times (possibly after being cut to a shorter length). FIG. 27 shows this configuration after hook panel 20 has been secured to the outward facing portion of the strap.

The inventive wrap system can be combined with the thermal packs in additional ways that have not been illustrated. The following paragraphs provide additional examples:

1. The cold packs can be replaced with hot packs containing thermal media that are designed to be heated in a microwave.
2. The hook material and the loop material can be reversed in most any situation.
3. Inelastic material can be used for the strap where desired.
4. The hook panel can be placed on either strap or on the body itself in some circumstances.
5. One or more air bladders can be added in addition to the thermal packs, or in some instances combined with the thermal packs. Air bladders are disclosed in detail in commonly-owned U.S. patent application Ser. No. 16/427,457.
6. The aforementioned air bladders can be provided with hook panels so that a user can place them on a desired interior surface of the universal wrap.
7. A coolant circulation bladder can be added in addition to the thermal packs or in the place of some or all of the thermal packs. An external circulation pump and cooling system can be used with the coolant circulation bladder. As for the air bladder, a coolant circulation bladder can be provided with hook panels so that a user can place them on a desired interior surface of the universal wrap.

Although the preceding descriptions present considerable detail they should be properly viewed as illustrating embodiments of the present invention rather than limiting the scope of the invention. Many more embodiments following the same principles will occur to those skilled in the art. Accordingly, the scope of the invention should be fixed by the following claims rather than by the examples given.

Having described my invention, I claim:

1. A method for applying a thermal pack to an affected region of a patient, comprising:
   (a) providing a universal wrap, including,
      (i) a body, having a first edge and a second edge opposite said first edge,
      (ii) said body including an inner surface covered in hook-compatible material,
      (iii) a strap connected to said first edge of said body, with said strap having an outer surface,
      (iv) a tab connected to said second edge of said body, said tab including a hook surface and a back surface, with said tab being configured to fold over said inner surface of said body with said hook surface on said tab engaging said hook-compatible material on said inner surface of said body,
      (v) a hook panel;
   (b) providing a thermal pack, including,
      (i) an outer layer,
      (ii) an inner layer,
      (iii) an interior volume containing thermal media,
      (iv) a hook panel on said outer layer;
   (c) cutting said strap to form a first segment and a second segment;
   (d) exposing said hook surface of said tab;
   (e) pressing said outer surface of said second segment against said hook surface of said tab to connect said second segment to said tab, said second segment then having a proximal end connected to said tab and a distal end that is free;
   (f) said first segment having a proximal end that is connected to said first edge of said body and a distal end that is free;
   (g) affixing said thermal pack to said body by pressing said hook panel on said outer layer of said thermal pack against said inner surface of said body;
   (h) positioning said thermal pack over said affected region of said patient with said thermal pack lying between said affected region of said patient and said body;
   (i) passing said first and second segments around a portion of said patient's anatomy that is opposite said affected region; and
   (j) using said hook panel to connect said distal end of said first segment to said distal end of said second segment.

2. The method for applying a thermal pack to said affected region of a patient as recited in claim 1, wherein said thermal media of said thermal pack comprises:
   (a) discrete hydrophilic absorber granules; and
   (b) a solution of water and a humectant.

3. The method for applying a thermal pack to said affected region of a patient as recited in claim 2, wherein:
   (a) said humectant is selected from the group consisting of propylene glycol, ethylene glycol, glycerin, dimethyl sulfoxide, dimethyl formamide, and combinations thereof; and
   (b) said discrete hydrophilic absorber granules are comprised of acrylic polymer.

4. The method for applying a thermal pack to said affected region of a patient as recited in claim 3, comprising adjusting a length of one of said first segment and said second segment so that said hook panel lies in a convenient position for said patient to grasp.

5. The method for applying a thermal pack to said affected region of a patient as recited in claim 2, wherein said thermal media further comprises a plurality of sub-bags filled with water.

6. The method for applying a thermal pack to said affected region of a patient as recited in claim 5, comprising adjusting a length of one of said first segment and said second segment so that said book panel lies in a convenient position for said patient to grasp.

7. The method for applying a thermal pack to said affected region of a patient as recited in claim 2, comprising adjusting a length of one of said first segment and said second segment so that said hook panel lies in a convenient position for said patient to grasp.

8. The method for applying a thermal pack to said affected region of a patient as recited in claim 1, wherein said body of said universal wrap is made of soft fabric.

9. The method for applying a thermal pack to said affected region of a patient as recited in claim 8, comprising adjusting a length of one of said first segment and said second segment so that said hook panel lies in a convenient position for said patient to grasp.

10. The method for applying a thermal pack to said affected region of a patient as recited in claim 1, comprising adjusting a length of one of said first segment and said second segment so that said hook panel lies in a convenient position for said patient to grasp.

11. A method for applying a thermal pack to an affected region of a patient, comprising:
   (a) providing a universal wrap, including,
      (i) a body, having a first edge and a second edge opposite said first edge,
      (ii) said body including an inner surface covered in hook-compatible material,
      (iii) a strap connected to said first edge of said body, with said strap having an outer surface,
      (iv) a tab connected to said second edge of said body, said tab including a hook surface and a back surface;
      (v) a hook panel;
   (b) providing a thermal pack, including,
      (i) an outer layer,
      (ii) an inner layer,
      (iii) an interior volume containing thermal media,
      (iv) a hook panel on said outer layer;
   (c) cutting said strap to form a first segment and a second segment;
   (d) pressing said outer surface of said second segment against said hook surface of said tab to connect said second segment to said tab, said second segment then having a proximal end connected to said tab and a distal end that is free;
   (e) said first segment having a proximal end that is connected to said first edge of said body and a distal end that is free;
   (f) affixing said thermal pack to said body by pressing said hook panel on said outer layer of said thermal pack against said inner surface of said body;
   (g) positioning said thermal pack over said affected region of said patient with said thermal pack lying between said affected region of said patient and said body;
   (h) passing said first and second segments around a portion of said patient's anatomy;
   (i) applying tension to said first and second segments, and
   (j) using said hook panel to connect said distal end of said first segment to said distal end of said second segment, thereby urging said thermal pack against said affected region.

12. The method for applying a thermal pack to said affected region of a patient as recited in claim 11, wherein said thermal media of said thermal pack comprises:
   (a) discrete hydrophilic absorber granules; and
   (b) a solution of water and a humectant.

13. The method for applying a thermal pack to said affected region of a patient as recited in claim 12, wherein:
   (a) said humectant is selected from the group consisting of propylene glycol, ethylene glycol, glycerin, dimethyl sulfoxide, dimethyl formamide, and combinations thereof; and
   (b) said discrete hydrophilic absorber granules are comprised of acrylic polymer.

14. The method for applying a thermal pack to said affected region of a patient as recited in claim 13, comprising adjusting a length of one of said first segment and said second segment so that said hook panel lies in a convenient position for said patient to grasp.

15. The method for applying a thermal pack to said affected region of a patient as recited in claim 12, wherein said thermal media further comprises a plurality of sub-bags filled with water.

16. The method for applying a thermal pack to said affected region of a patient as recited in claim 15, comprising adjusting a length of one of said first segment and said second segment so that said hook panel lies in a convenient position for said patient to grasp.

17. The method for applying a thermal pack to said affected region of a patient as recited in claim 12, comprising adjusting a length of one of said first segment and said second segment so that said hook panel lies in a convenient position for said patient to grasp.

18. The method for applying a thermal pack to said affected region of a patient as recited in claim 11, wherein said body of said universal wrap is made of soft fabric.

19. The method for applying a thermal pack to said affected region of a patient as recited in claim 18, comprising adjusting a length of one of said first segment and said second segment so that said hook panel lies in a convenient position for said patient to grasp.

20. The method for applying a thermal pack to said affected region of a patient as recited in claim 11, comprising adjusting a length of one of said first segment and said second segment so that said hook panel lies in a convenient position for said patient to grasp.

* * * * *